(12) United States Patent
Mangan et al.

(10) Patent No.: US 7,671,975 B2
(45) Date of Patent: Mar. 2, 2010

(54) BLOOD PROCESSING APPARATUS WITH DEDICATED STROBOSCOPIC CONTROLLER FOR LED SOURCE

(75) Inventors: Charles Patrick Mangan, Castle Rock, CO (US); Jeremy Kolenbrander, Brighton, CO (US)

(73) Assignee: CaridianBCT, Inc., Lakewood, CO (US)

( * ) Notice: Subject to any disclaimer, the term of this patent is extended or adjusted under 35 U.S.C. 154(b) by 590 days.

(21) Appl. No.: 11/613,338

(22) Filed: Dec. 20, 2006

(65) Prior Publication Data
US 2007/0085996 A1    Apr. 19, 2007

Related U.S. Application Data

(63) Continuation-in-part of application No. 10/905,353, filed on Dec. 29, 2004, now Pat. No. 7,327,443, which is a continuation-in-part of application No. 10/884,877, filed on Jul. 1, 2004, now Pat. No. 7,422,693.

(51) Int. Cl.
    *G01N 33/48* (2006.01)
(52) U.S. Cl. ........................................ 356/39
(58) Field of Classification Search ............ 356/39
    See application file for complete search history.

(56) References Cited

U.S. PATENT DOCUMENTS

| | | | |
|---|---|---|---|
| 4,151,844 A | 5/1979 | Cullis et al. |
| 4,493,691 A | 1/1985 | Calari |
| 4,557,719 A | 12/1985 | Neumann et al. |
| 4,670,002 A | 6/1987 | Koreeda et al. |
| 4,724,317 A | 2/1988 | Brown et al. |
| 4,834,890 A | 5/1989 | Brown et al. |
| 5,076,911 A | 12/1991 | Brown et al. |
| 5,104,526 A | 4/1992 | Brown et al. |
| 5,159,268 A | 10/1992 | Wu |
| 5,260,598 A | 11/1993 | Brass et al. |
| 5,316,667 A | 5/1994 | Brown et al. |
| 5,322,620 A | 6/1994 | Brown et al. |

(Continued)

FOREIGN PATENT DOCUMENTS

DE        3413065        10/1984

(Continued)

OTHER PUBLICATIONS

International Search Report and Written Opinion for PCT/US2004/021344, Jun. 12, 2008.

(Continued)

*Primary Examiner*—Roy Punnoose
(74) *Attorney, Agent, or Firm*—John R. Merkling; Edna M. O'Connor; Laura B. Arciniegas

(57) ABSTRACT

A centrifuge blood processing system for separating fluid components comprising a first light source comprising a plurality of light emitting diodes in optical communication with the centrifuge blood processing system for providing an incident light beam for illuminating an observation region on the centrifuge blood processing system, a light collection element in optical communication with the centrifuge blood processing system for collecting at least a portion of the light transmitted, scattered or both from the observation region, a programmable controller for providing an operational procedure for the monitoring system; and an independent dedicated control circuit in electrical communication with the programmable controller and electrically coupled to the light source, the control circuit receiving command parameters from the controller and controlling periods of illumination from the light source in response to the command parameters. Periods of illumination are controlled to prevent the failure of LEDs.

63 Claims, 13 Drawing Sheets

U.S. PATENT DOCUMENTS

| | | | |
|---|---|---|---|
| 5,653,887 | A | 8/1997 | Wahl et al. |
| 5,814,279 | A | 9/1998 | Biesel et al. |
| 6,053,856 | A | 4/2000 | Hlavinka |
| 6,262,799 | B1 * | 7/2001 | Wardlaw .................. 356/39 |
| 6,334,842 | B1 | 1/2002 | Hlavinka et al. |
| 6,514,189 | B1 | 2/2003 | Hlavinka et al. |
| 6,770,883 | B2 * | 8/2004 | McNeal et al. ........... 250/341.1 |
| 6,790,371 | B2 | 9/2004 | Dolecek |
| 2002/0147094 | A1 | 10/2002 | Dolecek |
| 2005/0051446 | A1 | 3/2005 | Carter et al. |
| 2006/0001860 | A1 | 1/2006 | Scibona et al. |

FOREIGN PATENT DOCUMENTS

| | | |
|---|---|---|
| DE | 3301113 | 1/1985 |
| EP | 0 392 475 | 10/1990 |
| EP | 0 729 790 | 5/2001 |
| WO | WO96/39618 | 5/1996 |

OTHER PUBLICATIONS

Zhou et al, "FPGA Implementation of a New Hybrid Rotor Position Estimation Scheme Based on Three symmetrical Locked Hall Effect position Sensors", Power Electronics and Motion Control Conference, 2004, IPEMC2004, v. 3, pp. 1592-1596.

International Search Report for PCT/US2004/021344.

Salgaller, Michael, "A Manifesto on the Current State of Dendritic Cells in Adoptive Immunotherapy", *Transfusion* 43(4):422-424, 2003.

* cited by examiner

BLOOD PROCESSING APPARATUS WITH DEDICATED STROBOSCOPIC CONTROLLER FOR LED SOURCE

CROSS-REFERENCE TO RELATED APPLICATIONS

This application is a continuation-in-part of U.S. patent application Ser. No. 10/905,353, filed Dec. 29, 2004, now U.S. Pat. No. 7,327,443, which is a continuation-in-part of U.S. patent application Ser. No. 10/884,877, filed Jul. 1, 2004, now U.S. Pat. No. 7,422,693, both of which are hereby incorporated by reference in their entirety to the extent not inconsistent with the disclosure herein.

BACKGROUND OF INVENTION

Blood collection and processing play important roles in the worldwide health care system. In conventional blood collection, blood is removed from a donor or patient, separated into its various blood components via centrifugation, filtration and/or elutriation and stored in sterile containers for future infusion into a patient for therapeutic use. The separated blood components typically include fractions corresponding to red blood cells, white blood cells, platelets and plasma. Separation of blood into its components can be performed continuously during collection or can be performed subsequent to collection in batches, particularly with respect to the processing of whole blood samples. Separation of blood into its various components under highly sterile conditions is critical to most therapeutic applications.

Recently, apheresis blood collection techniques have been adopted in many blood collection centers wherein a selected component of blood is collected and the balance of the blood is returned to the donor during collection. In apheresis, blood is removed from a donor and immediately separated into its components by on-line blood processing methods. Typically, on-line blood processing is provided by centrifugation, filtration and/or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Alternatively, apheresis techniques may be used to perform red blood cell exchange for patients with hematological disorders such as sickle cell anemia and thalassemia, whereby a patient's red blood cell component is removed and donated packed red blood cells are provided to the patient along with his remaining blood components. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber, which is rotated at high rotational speeds about a central rotation axis. Rotation of the separation chamber creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. patent application Ser. No. 10/413,890.

To achieve continuous, high throughput blood separation, extraction or collection ports are provided in most separation chambers. Extraction ports are capable of withdrawing material from the separation chamber at adjustable flow rates and, typically, are located at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the separation chamber, thereby degrading the extent of separation achieved during blood processing. Although conventional blood processing via centrifugation is capable of efficient separation of individual blood components, the purities of individual components obtained using this method is often not optimal for use in many therapeutic applications. For example, centrifugation separation of blood samples is unable to consistently (99% of the time) produce separated platelet components which have less than $1 \times 10^6$ white blood cells per every $3 \times 10^{11}$ platelets collected. The presence of white blood cells in platelet products increases the risks of viral exposure and immunological complications upon infusion into a patient.

The purity of extracted blood components using centrifugation is currently limited by the control of the position of phase boundary layers between separated components provided by conventional centrifugation devices and methods. The position of phase boundaries along the separation axis depends on a number of variables. First, phase boundary positions depend on the relative flow rates of individual blood components out of the separation chamber. Second, phase boundary positions depend on the rotational velocity of the separation chamber about the central rotation axis and the temperature of the blood undergoing separation. Third, phase boundary positions vary with the composition of the blood undergoing processing. Blood sample composition may vary considerably from donor to donor and/or from patient to patient. In addition, blood composition may vary significantly as function of time for a given donor or patient, especially as blood is recycled through the separation chamber multiple times. Given the sensitivity of the phase boundary position to many variables, which change from person to person and during processing, it is important to monitor the position of the phase boundaries during blood processing to ensure optimal separation conditions are maintained and the desired purity of selected blood components is achieved. In addition, accurate characterization of the positions of phase boundaries allows for separation conditions to be adjusted and optimized for changes in blood composition during processing.

It will be appreciated from the foregoing that a need exists for methods and devices for monitoring and controlling the processing of whole blood samples and blood component samples. Particularly, optical monitoring methods and devices are needed which are capable of accurately characterizing the separation, extraction and collection of blood components processed by centrifugation, including providing controlled stroboscopic light sources with consistent duration and intensity of illumination.

SUMMARY OF THE INVENTION

This invention provides stroboscopic LED light sources for use with devices for improving the processing of fluids, such as blood, components of blood and fluids derived from blood.

In one aspect, this invention provides methods, devices and device components for improving the separation of whole blood via centrifugation and subsequent collection of selected, separated blood components. Particularly, the invention relates to optical methods, devices and device components for stroboscopic light sources for light to be transmitted and/or scattered by separated blood components in a rotating separation chamber, particularly a separation chamber having an optical cell with one or more extraction ports.

The invention relates to an apparatus for controlling the processing of blood into blood components, particularly components for stroboscopic LED light sources for centrifuges. The stroboscopic apparatus comprises a first light source with reflective surfaces spaced around a central illumination axis, and light-emitting diodes spaced away from the axis radially outward from the reflective surfaces. An additional light source comprises a modified parabolic reflector surrounding a light emitting diode, the parabolic reflector having walls spaced outwardly from an axis of symmetry such that focal points fall radially outwardly from a center of the LED, forming a circular focal area. A controller that energizes the diodes for selected periods of time comprises a pair of switches connected in series, with an LED connected between the switches. One of the switches is connected to ground and is closed at the end of a period of illumination.

An exemplary optical monitoring system for a centrifuge having a separation chamber rotating about a central rotation axis comprises at least one light source, a light collection element and a detector. Rotation of the separation chamber about a central rotation axis results in separation of the blood components in the separation chamber according to density along rotating separation axes oriented perpendicular to the central rotation axis of the centrifuge. Both the light source and light collection element are arranged such that they are periodically in optical communication with an observation region positioned on the centrifuge. In one embodiment, the light source and detector are arranged such that an optical cell of the separation chamber is periodically rotated into and out of the observation region. The light source is capable of providing an incident light beam which illuminates at least a portion of the centrifuge, preferably an optical cell of the rotating separation chamber, thereby generating light which is transmitted, scattered, or both, by blood components undergoing separation. Preferred light sources are capable of generating an incident light beam having a selected wavelength range including, but not limited to, visible light, infrared light and/or ultraviolet light. In one embodiment, a plurality of light sources is provided capable of illuminating a plurality of sides of an optical cell of a separation chamber.

The light collection element is capable of collecting light from an observation region. In one embodiment, collected light from the observation region corresponds to light which is transmitted and/or scattered by blood components undergoing separation, light which is transmitted and/or scattered by components of the centrifugation device, such as the separation chamber, or both. The light collection element directs the collected light onto the detector. The detector may also be capable of generating one or more output signals corresponding to the distribution of transmitted and/or scattered light intensities from the observation region. The output signal may be transmitted to a device, such as a computer, capable of displaying the distribution of intensities, storing the distribution of intensities and/or processing the distribution of intensities.

The invention is further illustrated by the following description, examples, drawings and claims.

DETAILED DESCRIPTION OF THE INVENTION

Figure 1:
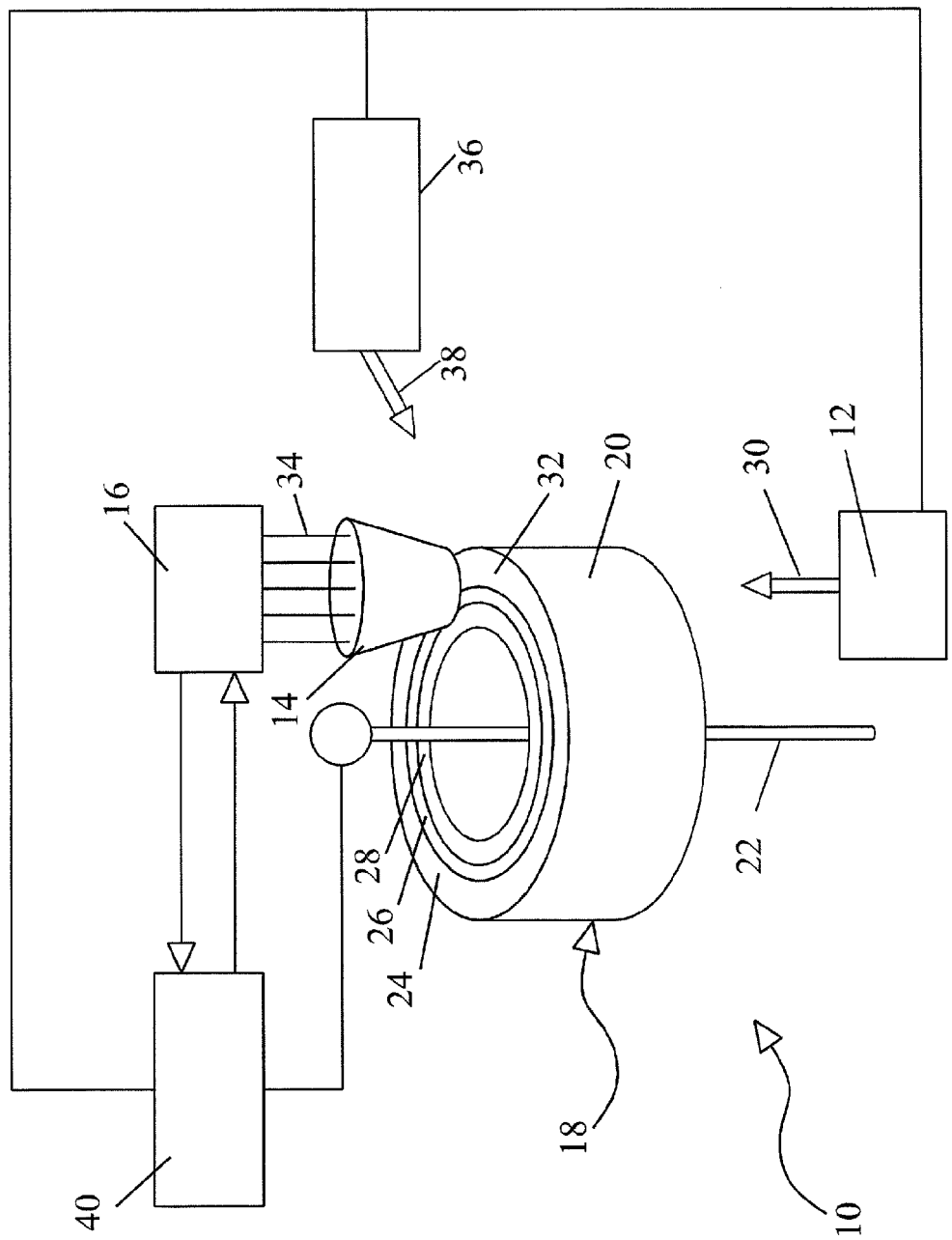
FIG. 1 is a schematic drawing showing an optical monitoring and control system of the present invention.

Referring to the drawings, like numerals indicate like elements and the same number appearing in more than one drawing refers to the same element. In addition, hereinafter, the following definitions apply:

The terms "light" and "electromagnetic radiation" are used synonymously and refer to waves of electric and magnetic fields that also exhibit particle-like behavior. Light useful for the methods of the present invention includes gamma rays, X-rays, ultraviolet light, visible light, infrared light, microwaves, radio waves or any combination of these.

"Light collection element" refers to a device or device component that collects light and distributes the collected light in a desired way. Light collection elements useable in the present invention are capable of collecting at least a portion of transmitted light, scattered light or both generated upon illumination of an observation region on a blood-processing device. Exemplary light collection elements of the present invention are capable of collecting light in a manner generating an image of an observation region on a detector. Light collection elements of the present invention include, but are not limited to, fixed focus lenses, spherical lenses, cylindrical lenses, aspheric lenses, wide angle lenses, zoom lenses, concave lenses, convex lenses, biconcave lenses, biconvex lenses, lens systems comprising a plurality of lenses, wave guides, fiber optic couplers, reflectors, spherical mirrors, aspherical mirrors, prisms, apertures, lenses, or any combination or equivalents of these. Light collection elements of the present invention are capable of directing collected light onto another optical device or device component, such as a detector. Light collection elements include at least one lens system having a selectively adjustable field of view and/or focal length. Light collection elements can be translatable along a detection axis, which is perpendicular to a central rotation axis.

"Field of view" refers to the angular distribution of light rays, which are collected and detected by an optical detection system, such as a light collection element in optical communication with a detector. Optical detection systems of the present invention can have a fixed field of view or a field of view that is selectively adjustable.

"Blood processing" refers to the manipulation of a blood sample or component thereof, to realize a change in composition. Blood processing includes methods of separating blood or a component thereof into components or subcomponents, leukoreduction, pathogen inactivation, blood filtering, oxygenating blood and blood components, dialysis, blood purification or clearing, pathogen removal, blood and blood component warming, blood component washing, and red blood cell deglycerolization. The present invention provides improved methods of blood processing wherein a blood sample or component thereof is separated into components or subcomponents on the basis of density, size, diffusion rate, sedimentation velocity, surface chemistry properties or combinations of these characteristics.

"Observation region" refers to an illuminated portion of an object or plurality of objects. At least a portion of transmitted light, scattered light or both from the observation region is collected by a light collection element and detected by a detector. In preferred embodiments of the present invention, the observation region is positioned on a blood-processing device, component of a blood-processing device, such as an optical cell, or a blood sample container. The size and position of the observation region is determined by the field of view of the light collection element, the position of the light collection element from the blood processing device, the area of the detector and the position of the detector with respect to the light collection element. In an embodiment, the size, shape and position of the observation region is selectively adjustable by controlling the position of the light collection element with respect to the blood processing device and the field of view of the light collection element. In an embodiment of the present invention, one or more phase boundaries between optically differentiable components are viewable in the observation region. In another preferred embodiment, at least one separated component is viewable in the observation region. In another preferred embodiment, at least one extraction port is viewable in the observation region.

"Blood sample" and "blood" are used synonymously to refer to whole blood, one or more blood component, one or more blood products, or any combination of these. "Blood component" and "blood product" as used herein include cellular components, non-cellular components of blood and combinations of cellular and non-cellular components of blood. Exemplary cellular components include but are not limited to erythrocytes (red blood cells), leukocytes (white blood cells), and thromobocytes (platelets) and combinations of these materials. Leukocytes comprise monocytes, granulocytes, agranulocytes, and lymphocytes. Exemplary non-cellular components include but are not limited to plasma, dissolved salts and minerals and plasma proteins. A blood component can be further fractionated into blood sub-components.

"Epi-illumination" refers to the illumination of an object and generation of scattered light. In epi-illumination, light is directed to the object along an axis of illumination that is different than the optical axis whereby scattered light is collected and detected.

"Parallel", in a physical, non-electrical sense, refers to a geometry in which two surfaces are equidistant from each other at all points and have the same direction or curvature. Substantially parallel refers to a geometry in which angular deviations from absolute parallelism are less than 10 degrees, and preferably less than 0.5 degrees for some applications.

In the following description, numerous specific details of the devices, device components and methods of the present invention are set forth in order to provide a thorough explanation of the precise nature of the invention. It will be apparent, however, to those of skill in the art that the invention can be practiced without these specific details. Reference in the specification to "a preferred embodiment," "a more preferred embodiment" or "an exemplary embodiment" means that a particular feature, structure, or characteristic set forth or described in connection with the embodiment is included in at least one embodiment of the invention. References to "preferred embodiment," "a more preferred embodiment" or "an exemplary embodiment" in various places in the specification do not necessarily refer to the same embodiment.

FIG. 1 schematically illustrates an exemplary embodiment of the optical monitoring system of the present invention capable of measuring a distribution of scattered and/or transmitted light intensities corresponding to patterns of light originating from an observation region on a separation chamber. The illustrated monitoring system 10 comprises light source 12, light collection element 14, and detector 16. Light source 12 is in optical communication with a centrifuge 18 comprising separation chamber 20, which rotates about central rotation axis 22. Rotation about central rotation axis 22 results in separation of a blood sample in the separation chamber into discrete blood components along a plurality of rotating separation axes oriented orthogonal to the central rotation axis 22. In a preferred embodiment, separation chamber 20 is held in a circular filler (not shown in FIG. 1), which is also capable of rotation about central rotation axis 22. The filler may comprise a disc having an internal, circular groove wherein the separation chamber is positioned and fastened. During operation of the centrifuge, the filler is operationally connected to a rotating means such that both filler and separation chamber are rotated about the central rotation axis 22. In the schematic shown in FIG. 1, the blood sample is separated into an outer higher density phase corresponding to a red blood cell component 24, an intermediate density phase corresponding to a white blood cell and platelet-containing component (e.g. buffy coat) 26 and a lower density inner phase corresponding to a platelet enriched plasma component 28.

Light source or sources 12, 36 provide incident light beams 30, 38, which illuminate an observation region 32 on separation chamber 20, preferably in a manner generating scattered and/or transmitted light from the blood sample undergoing separation. In one embodiment, light source 12 is capable of generating an incident light beam, a portion of which is transmitted through at least one blood component undergoing separation in separation chamber 20. At least a portion of scattered and/or transmitted light 34 from the observation region 32 is collected by light collection element 14. Light collection element 14 is capable of directing at least a portion of the collected light 34 onto detector 16. The detector 16 detects patterns of scattered and/or transmitted light 34 from the observation region, thereby measuring distributions of scattered and/or transmitted light intensities. In an exemplary embodiment, distributions of scattered and/or transmitted light intensities comprise images corresponding to patterns of light originating from the observation region 32. In one embodiment, images of the present invention are monochrome images, which provide a measurement of the brightness of separated blood components along the separation axis. Alternatively, images of the present invention are color images, which provide a measurement of the colors of separated blood components along the separation axis.

Observation region 32 is positioned on a portion of the centrifuge 18, preferably on the separation chamber 20. In the exemplary embodiment illustrated in FIG. 1, separated blood components and phase boundaries between optically differentiable blood components are viewable in observation region 32. In one embodiment, the observation region is positioned on an optical cell of the separation chamber having windows for transmitting the incident beam through the blood sample undergoing processing. In an alternative preferred embodiment, one or more extraction ports (not shown in FIG. 1) are viewable in observation region 32. In another embodiment, observation region 32 is positioned on the top of the separation chamber 20 such that leaks of the blood sample and/or improper alignment of the separation chamber or filler are viewable. In another alternative embodiment, the observation region 32 is positioned on a portion of the separation chamber such that the composition of a separated blood component can be directly monitored. For example, a monitoring system of the present invention provides a method of characterizing the type of cellular component collected and counting the amount of cells extracted from the separation chamber as a function of time. Alternatively, the monitoring system is arranged such that the concentration of non-cellular blood components, such as blood plasma proteins, is directly measured. In one embodiment, the observation region 32 is arranged such that a plurality of measurements is obtained from every measured distribution of scattered and/or transmitted light intensities.

Optionally, the observation region 32 can also be illuminated by epi-illumination light source 36, which is positioned on the same side of the separation chamber as the light collection element and detector. Epi-illumination light source 36 is positioned such that it generates an incident beam 38, which is scattered by the blood sample and/or centrifuge. A portion of the light from epi-illumination light source 36 scattered by the separation chamber and is collected by light collection element 14 and detected by detector 16, thereby measuring a distribution of scattered and/or transmitted light intensities.

In one embodiment, detector 16 is also capable of generating output signals corresponding to the measured distributions of scattered and/or transmitted light intensities and/or images. In the exemplary embodiment shown in FIG. 1, detector 16 is operationally connected to a centrifugation device controller 40 capable of receiving the output signals. In one embodiment, centrifugation device controller 40 displays the measured intensity distributions, stores the measured intensity distributions, processes measured intensity distributions in real time, transmits control signals to various optical and mechanical components of the monitoring system and centrifuge or any combination of these. In a preferred embodiment, centrifugation device controller 40 is operationally connected to centrifuge 18 and is capable of adjusting selected operating conditions of the centrifuge, such as the flow rates of cellular and non-cellular components out of the separation chamber, the position of one or more phase boundaries along the separation axes, rotational velocity of the separation chamber about central rotation axis 22, the infusion of anticoagulation agents or other blood processing agents to the blood sample, or any combination of these.

As shown in FIG. 1, centrifugation device controller 40 can also be operationally connected to light source 12 and/or epi-illumination light source 36. In this embodiment, centrifugation device controller 40 and/or detector 16 are capable of generating output signals for controlling illumination conditions. For example, output signals from detector can be used to control the timing of illumination pulses, illumination intensities, the distribution of illumination wavelengths and/or position of light source 12 and/or epi-illumination light source 36. As also shown in the embodiment illustrated in FIG. 1, centrifugation device controller and detector are in two-way communication. In this embodiment, centrifuge device controller sends control signals to detector 16 to selectively adjust detector exposure time, detector gain and to switch between monochrome and color imaging.

Light sources of the present invention comprise light emitting diode sources capable of generating one or more incident beams for illuminating an observation region on the centrifuge. A plurality of lamps may be positioned to illuminate a single side or multiple sides of a centrifuge. Light sources useable in the present invention include light emitting diodes and arrays of light emitting diode light sources. Use of light emitting diode light sources is preferred for some applications because they are capable of generating precisely timed illumination pulses. Preferred light sources generate an incident light beam having a substantially uniform intensity. In one embodiment, light sources of the present invention generate an incident beam having a selected wavelength range and selected intensity.

In a preferred embodiment, the optical monitoring system of the present invention comprises a plurality of light sources, each capable of generating an incident light beam having a different wavelength range. In one embodiment, for example, the optical monitoring system of the present invention comprises a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a red blood cell containing component is easily distinguished from platelet enriched plasma containing component by illumination with light having wavelengths selected over the range of about 500 nm to about 600 nm because the red blood cell component absorbs light over this wavelength significantly more strongly that the platelet enriched plasma containing component. In addition, use of multiple colored light sources for illumination provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

Light sources of the present invention provide a continuous incident light beam or a pulsed incident light beam. Pulsed light sources are capable of being switched on and off in a manner synchronous with the rotation of the separation chamber to provide distributions of transmitted and/or scattered light intensities corresponding to an observation region having a substantially fixed position using sensors, switches or other types of known cooperation. Alternatively, pulsed light sources of the present invention can be configured such that they can be switched on and off in a manner asynchronous with the rotation of the separation chamber providing distributions of transmitted and/or scattered light intensities corresponding to different observation regions for each full rotation. This alternative embodiment provides a method of selectively adjusting the location of the observation region and, thereby, probing different regions of the separation chamber. In one embodiment, triggering of illumination pulses is based on the rotational speed of the centrifuge or can be based on the angular position of the separation chamber as detected by optical or electronic methods well known in the art. In a preferred embodiment, trigger pulses generated by the centrifuge device controller and/or detector provide triggering.

Figure 2:
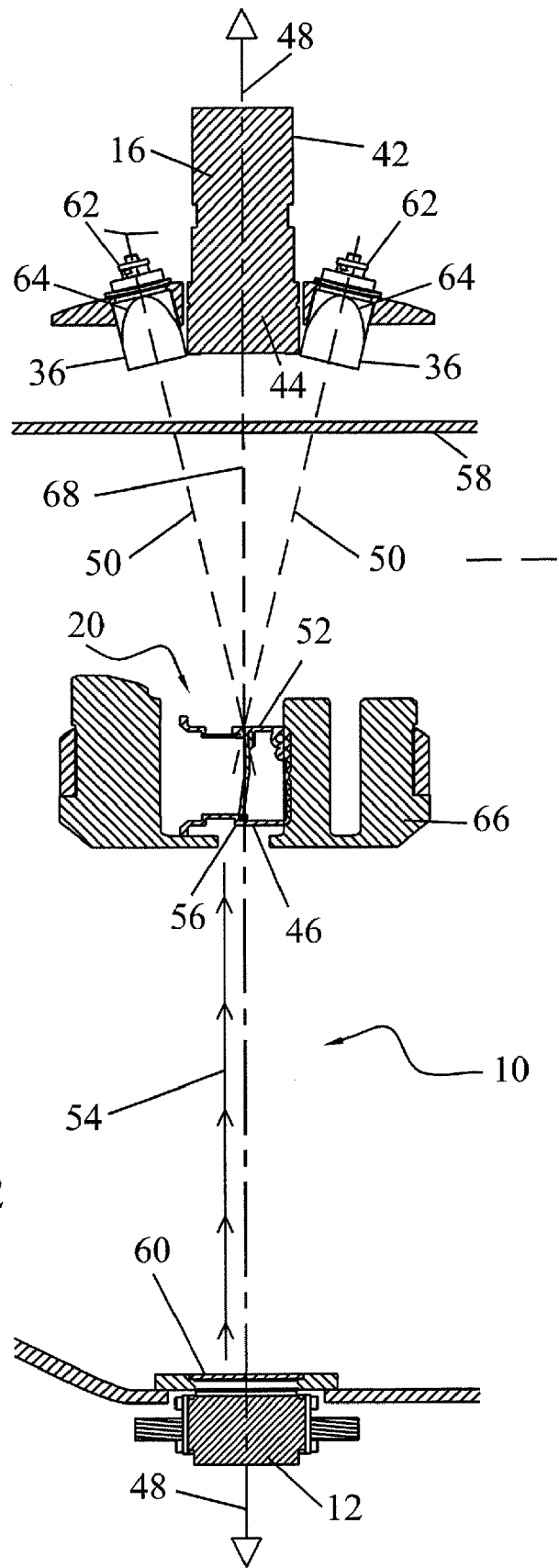
FIG. 2 is a cut away view of a separation chamber, camera and light sources.

The optical monitoring and control system comprises a light source, a close-focus lens system and a digital camera, arranged as illustrated in FIGS. 1 and 2. Illumination is provided by a light source positioned beneath the separation chamber. The light source is capable of directing light through a white blood cell extraction port of the optical cell. Illumination is also provided to the top of the optical cell. Light transmitted through and scattered by the optical cell is collected by the close focus lens system and detected by the digital camera. Distributions of transmitted and scattered light are acquired for each rotation or for every other rotation of the separation chamber or as selected.

Measurements generated from the operation of image-data analysis algorithms and process control algorithms may also serve as the basis of output signals sent to the camera and light collection element 14, and light sources 12, 36 and camera triggering hardware to optimize the quality of the images acquired and analyzed. For example, output signals can adjust in the intensity of the illumination beam, change the color of the illumination beam, or adjust the camera's gain or exposure time.

The present invention includes systems for monitoring and controlling blood processing via centrifugation that are capable of providing simultaneous real time measurements of the positions of phase boundaries between optically differentiable blood components relative to calibration markers and the compositions and/or fluxes of separated and extracted blood components. A system of the present invention exhibiting excellent sensitivity, mechanical ruggedness and reliability comprises a fixed position CCD camera 42 equipped with a fixed focus lens, a top pulsed LED (light emitting diode) light source and a bottom pulsed LED light source. Use of a fixed position CCD camera equipped with a fixed focus lens system provides a system exhibiting high mechanical stability with respect to maintaining optical alignment, which avoids the need for periodic adjustments of the optical path lengths illumination and detection beams. In addition, use of top and bottom pulsed LED light sources provides considerable flexibility in the wavelength distributions and intensities of illumination light beams directed onto the blood processing system and subsequently detected. Further, use of top and bottom pulsed LED light sources also provides accurate and reproducible temporal characteristics of illumination pulses useful for generating high optical quality images of a rotating optical cell of a separation chamber.

Figure 3:
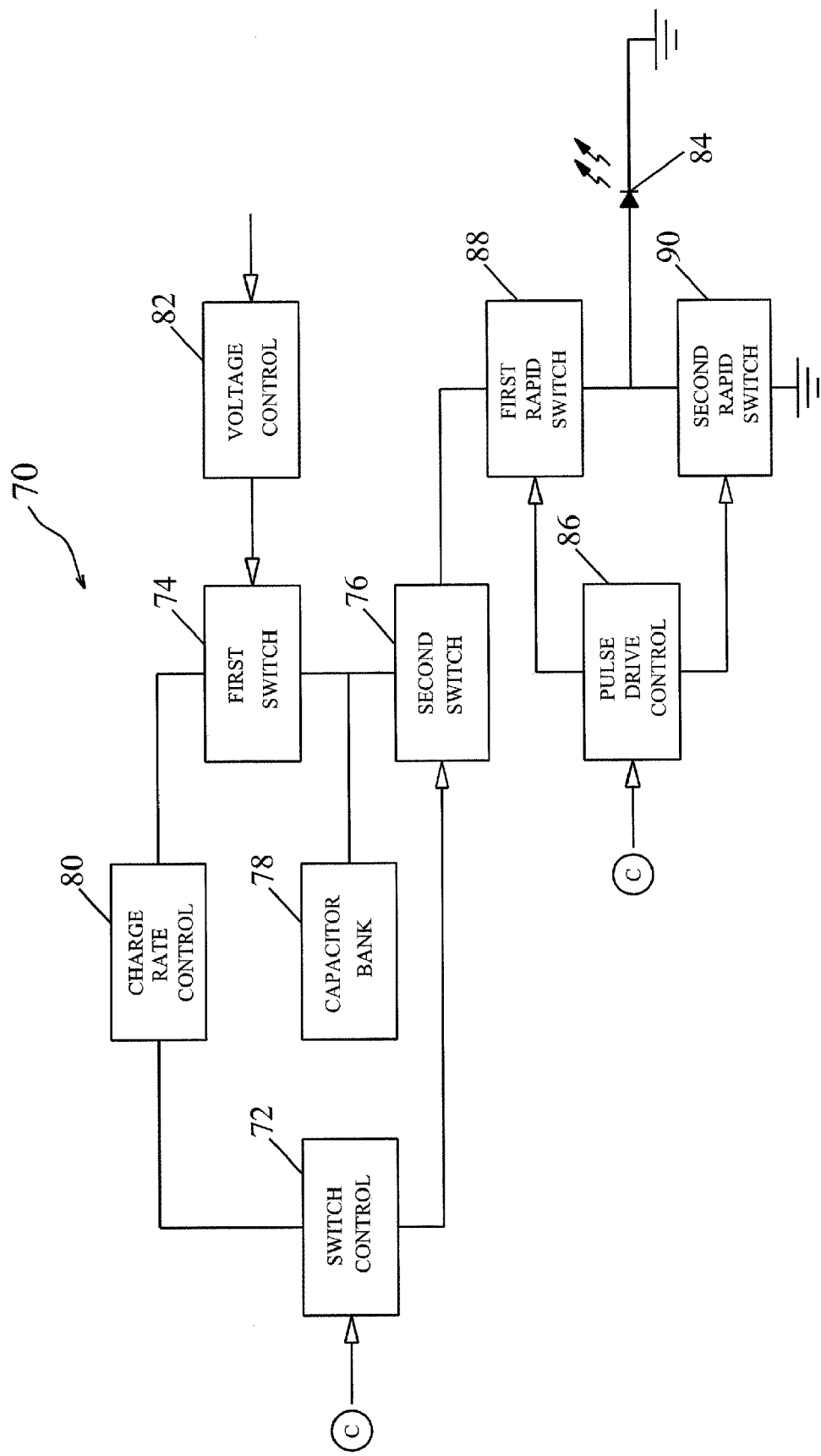
FIG. 3 is a functional block diagram of a control circuit.
Figure 4:
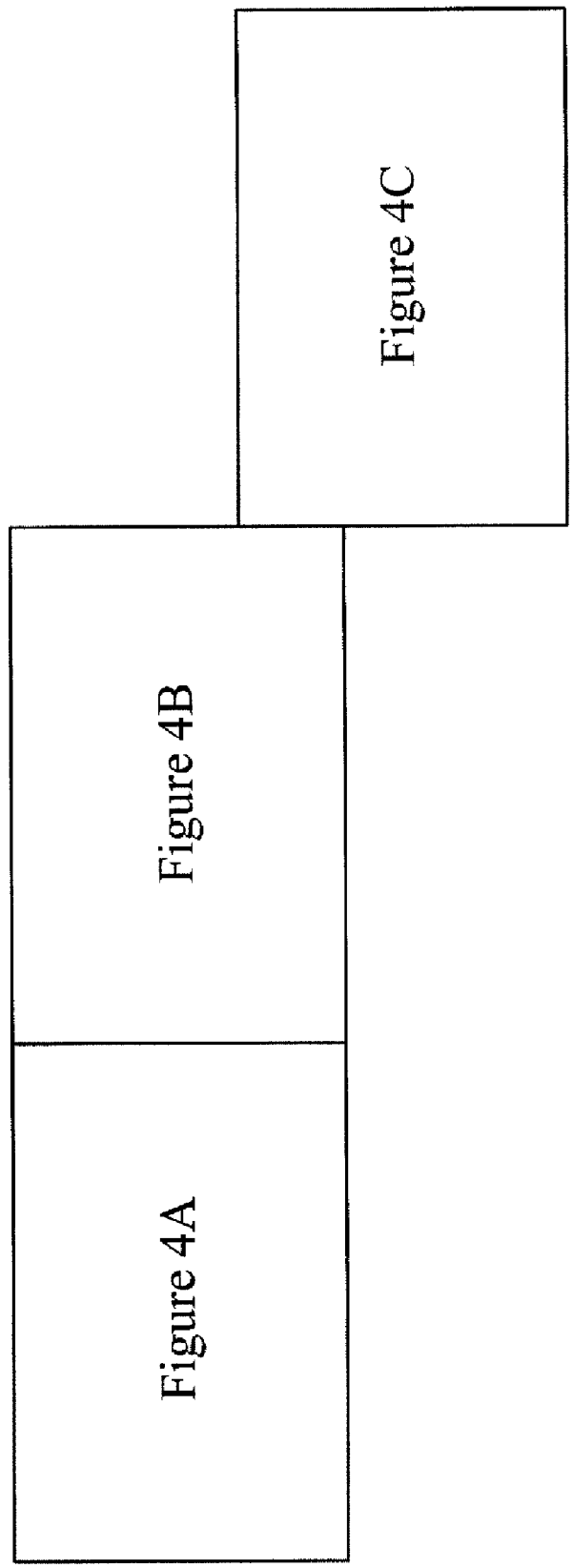
FIG. 4 shows the relationship of FIGS. 4A, 4B and 4C, which are schematic diagrams of the control circuit of FIG. 3.

FIG. 2 is a cut away view of a separation chamber 20, camera or detector 16 and light sources 12, 36. FIG. 4 is a perspective side view of the optical monitoring and control system illustrated in FIGS. 2 and 3. The illustrated optical monitoring and control system 10 comprises a CCD camera 42 equipped with a fixed focus lens system 44, an optical cell 46, a top pulsed LED light source 36, and a bottom pulsed LED light source 12. As illustrated in FIG. 3, CCD camera 42 with a fixed focus lens system 44 is in optical communication with optical cell 46 and positioned to intersect optical axis 48. Top pulsed LED light source 36 is in optical communication with optical cell 46 and is positioned such that it is capable of directing a plurality of collimated upper illumination light beams 50, propagating along propagation axes that intersect optical axis 48, onto the top side 52 of optical cell 46. Bottom pulsed LED light source 12 is also in optical communication with optical cell 46 and is positioned such that it is capable of directing a plurality of collimated bottom illumination light beams 54, propagating along a propagation axis parallel to optical axis 48, onto the bottom side 56 of optical cell 46.

In an exemplary embodiment, top pulsed LED light source 36 is positioned about 4.26 inches from the top 52 of optical cell 46, and bottom pulsed LED light source 12 is positioned about 7.47 inches from the top 52 of optical cell 46. In the exemplary embodiment shown in FIG. 3, CCD camera 42 with fixed focus lens system 44 is positioned such that the focal plane of fixed focus lens system is substantially co-planar with selected optical surfaces of optical cell 46, such as optical surfaces corresponding to an interface monitoring region, calibration markers, one or more extraction ports and one or more inlets. In this embodiment, the CCD camera 42 is also separated from the center of the fixed focus lens system by a distance along optical axis 48 such that an image corresponding to selected optical surfaces of optical cell 46 is provided on the sensing surface of the CCD camera 42. An advantage of this optical configuration is that it allows distributions of light intensities comprising images of top 52 of rotating optical cell 46 to be measured and analyzed in real time.

Referring to the cross section shown in FIG. 2, first transparent plate 58 is provided between CCD camera 42 with a fixed focus lens system 44 and optical cell 46, and second transparent plate 60 is provided between bottom pulsed LED light source 12 and optical cell 46. First and second transparent plates 58 and 60 physically isolate CCD camera 42 with a fixed focus lens system 44, top pulsed LED light source 36 and bottom pulsed LED light source 12 from optical cell 46 so that these components will not contact a sample undergoing processing in the event of sample leakage from the separation chamber.

Top pulsed LED light source 36 and bottom pulsed LED light source 12 in the optical monitoring and control system illustrated in FIG. 2 each comprise a plurality of LEDs, such as a LED array light source. Top pulsed LED light source 36 comprises multiple LEDs 62, each equipped with a parabolic reflector 64 to provide beam collimation.

LEDs useful for the top and bottom pulsed LED sources 36 and 12 can be red LEDs, green LEDs, white LEDs, infrared LEDs, ultraviolet LEDs or any combination of these. LEDs useful in the present invention provide collimated beams having intensities large enough allow measurement of intensity distributions comprising to images of optical cell 46. In an embodiment of the present invention, LED drive circuitry is optionally positioned proximate to top and/or bottom LED sources to optimize device performance.

Top pulsed LED light source 36 and bottom pulsed LED light source 12 are capable of providing synchronized light pulses having accurately selectable temporal characteristics. Pulse widths of light pulses useable in the present invention depend on the rotational velocity of the centrifuge. Typically, the smaller the pulse width of the light pulse, the less blurring of the optical image corresponding to the acquired distribution of light intensities. However, larger pulse widths allow more photons to be integrated by the CCD of the camera and, thus, provide enhanced signal-to-noise ratios. For a rotational velocity equal to about 3000 RPM, pulse widths less than about 8 microseconds are useful for minimizing blurring of the image of the optical cell generated. Exemplary light pulses useful for some applications of the present invention have pulse widths selected over the range of about 1 microsecond to about 50 microseconds.

In one embodiment, the CCD camera 42 comprises a monochrome or color CCD camera positioned a fixed, selected distance from a fixed focus lens system. CCD camera 42 and fixed focus lens system can be contained in a housing capable of maintaining the selected separation distance between these elements and also capable of minimizing detection of unwanted scattered light. An exemplary fixed focus lens system comprises a plurality of spherical lenses, cylindrical lenses, spacers or any combination of these elements. An exemplary CCD camera is the "Flea" manufactured by Point Grey Research, Inc. and has a pixel area equal to about 1024 pixels by 768 pixels. An exemplary lens comprises an F 2.8 fixed focal length lens system having a focal length of 28 millimeters manufactured by Linos Photonics. This combination of exemplary optical components provides a field of view equal to about 10 mm (3/8 inch) by 15 mm (1/2 inch) and a depth of field selected over the range of about 1.5 mm (1/16 inch) to about 15 mm (1/2 inch). This field of view and depth of field allows for measurement of distributions of light intensities comprising images of optical cell 46 useful for monitoring and controlling the positions of phase boundary positions in an interface region and the compositions of cellular material exiting one or more extraction port. Use of a CCD camera equipped with a fixed focus lens system enhances the mechanical stability of the system and is useful for maintaining selected relative orientations and positions of the CCD camera 42, fixed focus lens system and the optical cell. This aspect of the present invention provides the system with the ability to make highly reproducible measurements of the positions of phase boundary layers between optically differentiable, separated blood components in an interface region and the compositions of separated blood components exiting the optical cell through one or more extraction ports.

FIG. 2 also shows the optical path lengths provided by the present optical geometry. Top pulsed LED light source 36 generates a plurality of pulsed collimated upper illumination light beams 50 which propagate along propagation axes that intersect optical axis 48. At least a portion of the upper illumination light beams 50 passes through transparent plate 58 and is directed onto the top side 52 of optical cell 46. A portion of the upper illumination light beams 50 is scattered by optical cell 46, one or more separated blood components therein and/or a filler or rotor 66. Bottom pulsed LED source 12 generates a collimated bottom illumination light beams 54 which propagates along a propagation axis substantially parallel to optical axis 48. At least a portion of bottom illumination light beams 54 passes through transparent plate 60 and is directed onto the bottom side 56 of optical cell 46. A portion of bottom illumination light beams 54 is transmitted through optical cell 46 and one or more separated blood components therein. Light transmitted through optical cell 46 can correspond to an interface-monitoring region, one or more inlets, one or more extraction ports, one or more calibration markers or any combination of these.

Light 68 transmitted and/or scattered by optical cell 46 is collected by fixed focal length lens system and imaged onto the sensing surface of the CCD camera 42. In this manner, a distribution of light intensities is measured by CCD camera 42 that corresponds to an image of at least a portion of optical cell 46, such as the top 52 of optical cell 46. Detection of scattered light corresponding to the upper illumination light beams 50 is primarily used for system calibration, proximity identification and translational sensor tracking. Detection of transmitted light corresponding to the bottom illumination light beams 54 is primarily used for measurement of the position of one or more phase boundary layers of optically differentiable separated blood components in optical cell 46 and for measurement of the composition and flux of separated blood components exiting one or more extraction ports of optical cell 46. Detecting transmitted and scattered light arising from both top and bottom illumination maximizes the amount of information that can be extracted from an acquired distribution of light intensities and enhances the multifunctional capabilities of optical monitoring and control systems of the present invention.

Optionally, optical monitoring and control system 10 may further comprise one or more additional light detectors useful for optimizing the light levels of top and bottom pulsed LED light sources 36 and 12. In one embodiment, an additional light detector comprising a photodiode is provided which is capable of measuring scattered light from bottom pulsed LED light source 12. Use of an additional light detector capable of scattered light from bottom pulsed LED light source 12 is useful for trouble shooting and error handling aspects of the present invention.

The CCD camera 42 is capable of generating one or more output signals, corresponding to the measured distribution of light intensities. Output signals are sent to one or more centrifuge device controllers, such as a computer or processor, capable of analyzing the acquired distributions of transmitted and/or scattered light intensities and adjusting important operating conditions which affect separation conditions and the composition of extracted blood components. Selectively adjustable operating conditions include, but are not limited to, the rotational velocity of the centrifuge, the flow rates of one or more inlet pumps, and the flow rates of one or more extraction pumps, or any combination of these.

The optical monitoring and control system 10 is a pulsed optical system, whereby intensity distributions corresponding to optical cell 46 are acquired as it is rotated about the central rotational axis of the centrifuge 18. Intensity distributions can be acquired for every full rotation of optical cell 46 or can be acquired for selected rotations of optical cell 46, such as every other full rotation. Acquiring intensity distributions for every other rotation of optical cell 46 is beneficial for some applications because it avoids the need for costly CCD cameras capable of collecting more than about 30 frames per second and also minimizes spatial indication, calibration and optical imaging problems associated with reproducible instrument jitter observed upon rotation of the separation chamber.

To generate intensity distributions corresponding to good images of optical cell 46, top and bottom illumination pulse, camera shutter and gating settings and the rotation of optical cell 46 of a separation chamber of a centrifuge must be accurately synchronized. Accurate synchronization of these elements allows images of transmitted and/or scattered light intensities comprising high optical quality images of the optical cell to be measured for each full rotation or for selected rotations. In the present invention, the rotational position of components of the centrifuge and/or monitoring and control system, such as the optical cell or separation chamber, is accurately measured using an encoded motor system, as well known in the art. In an exemplary embodiment, centrifuge 18 is provided with any optical sensor capable of reading a plurality of markers on a rotating element of the centrifuge. This configuration allows for real time measurements of the rotational position of the optical cell, preferably measurements of rotational position accurate to about 0.09 degrees. This configuration also provides real time measurements of the rotational position of the optical cell when the rotational velocity changes, such as during spin up or spin down of the centrifuge.

The encoded motor system is also capable of generating output signals in real time corresponding to the rotational position of components of the centrifuge and/or monitoring and control system, such as the optical cell or separation chamber. In an exemplary embodiment, these output signals are provided as input to a synchronization and timing controller capable of sending one or more trigger signals to the top pulsed LED light source, bottom pulsed LED light source and the CCD camera 42. Trigger signals provided by the synchronization and timing controller to these device components include the trigger location (i.e. the time or rotational position for initiating to a light pulse), the trigger frequency (i.e. for which rotations should light pulses be generated), the pulse width setting (duration of light pulse) and the delay setting (i.e. time between when the trigger signal is received and when the light pulse is to be initiated). LED elements in top and bottom pulsed LED light sources and camera shutter and gate setting can be accurately triggered at times corresponding to a desired rotational position of the centrifuge using trigger signals generated by the synchronization and timing controller. Selection of the rotational position corresponding to the trigger signal allows the observation region to be selectively adjusted in the present invention. In this manner, a plurality of selected regions of the optical cell, separation chamber and other components of the centrifuge are optically probed.

In an exemplary embodiment, the exposure time of the CCD camera 42 is determined by the pulse width of the light pulses generated by the top and bottom pulsed LED light sources, rather than by the gating setting or shutter of the CCD camera 42. In one embodiment, the shutter of the CCD camera 42 can be opened longer than the light pulse duration without having significant background noise affects. As the pulse widths of light pulses generated by LED light sources can be controlled very accurately, this aspect of the present invention eliminates the need of costly CCD cameras providing very accurate gating corresponding to short exposure times.

In a preferred embodiment, each of the LED light sources are controlled by control circuits, such as control circuit 70, illustrated in functional block diagram in FIG. 3. A control circuit 70 may control all or any subset of the LED light sources. Preferably, however, a single control circuit controls two LED devices having the same frequency characteristics and positioned so that the failure of one LED device would not significantly affect the function of the apparatus as a whole. The control circuit 70 comprises a switch control unit 72 that selectively opens and closes a first switch circuit 74 and a second switch circuit 76 in response to signals from a microprocessor to maintain a selected charge on a bank 78 of power capacitors. The first switch circuit 74 is initially closed to charge the capacitor bank 78 while the second switch circuit 76 is open. A charging rate control circuit 80 limits the rate at which charge can be transferred to the capacitor bank 78. This prevents a sudden current demand as the system is initialized. Such a sudden demand might interfere with other power demands of the system as a whole. The charging rate may be fixed and not programmable, while other parameters of the control circuit 70 are programmable. The charging rate could be made programmable by using the digital potentiometer that adjusts the voltage stored on the capacitor bank 78. The microprocessor could then control charging by ramping the setting of the digital potentiometer at the programmed, controlled rate of change.

A voltage control circuit 82 regulates the peak voltage stored on the capacitor bank 78. The microprocessor selects the voltage stored on the capacitor bank 78 and preferably adjusts a digitally controllable device in the voltage control circuit. After the capacitor bank 78 is charged to its selected voltage, first switch circuit 74 can be left closed, allowing charging to continue during normal operation, and second switch circuit 76 can be closed, providing driving power to the LED devices through other circuit components, as explained below. The switch control unit 72 provides timing and control signals to close the first switch circuit 74 and to close the second switch circuit 76. When both switch circuits 74 and 76 are closed, power is established within the capacitor bank 78.

With second switch circuit 76 closed, power is available to the LED device or devices 84. Responsive to signals from the microprocessor, a pulse drive controller 86 controls first rapid response switch 88 and second rapid response switch 90, which bracket the LED device 84. Each of the rapid response switches 88, 90 is configured to turn on or off in such a manner to provide a well-defined square power wave to the LED device 84. With the second rapid response switch open, the first response switch can be closed to provide a path for current from the capacitor bank 78 through the LED device 84 to ground. As will be explained more fully below, the leading edge of the wave is well defined and abrupt and the voltage then remains relatively constant because of the substantial size of the capacitors in the capacitor bank 78. After the selected illumination period, the pulse drive controller 86 briefly turns off both switches 88, 90, as explained above in connection with the first and second switch circuits 74, 76, and then opens the second rapid response switch 90 to ground, draining any remaining power away from the LED device 84, and sharply and precisely turning the LED device 84 off.

The control circuit 70 produces a precisely controlled stroboscopic illumination. Both the duration and the magnitude (voltage) of the LED device output can be digitally controlled. This contrasts with xenon stroboscopic flash tubes, where the light-generating phenomenon is essentially an explosion, with an uncertain duration and an indeterminate intensity. In the preferred application for the present stroboscopic light, the target image is relatively far both from the light source and the detection device (video camera), but the phenomenon being detected, a boundary between fluid layers, is quite subtle. An intense yet consistent illumination is needed. Because the shutter speed of the camera is slower that the phenomenon being observed, the stroboscopic flash serves as the shutter for the optical system, and must, therefore, have both an abrupt beginning and end. These features are provided by the LED light sources and control circuits described herein.

Moreover, in the preferred application of the stroboscopic light, the limiting parameter tends to be the refresh rate for the video camera, which is generally limited to about 25-30 Hz, that is, one image for every second revolution of the rotor at higher rotor speeds. Because this cycle between images is relatively long compared to the period of illumination by the LED light sources, the control circuit 70 has ample time to fully recharge the capacitor bank 78 through first and second switch circuits 74, 76 before power is supplied to the LED device 84 through first and second rapid response switches 88, 90.

Figure 4A:
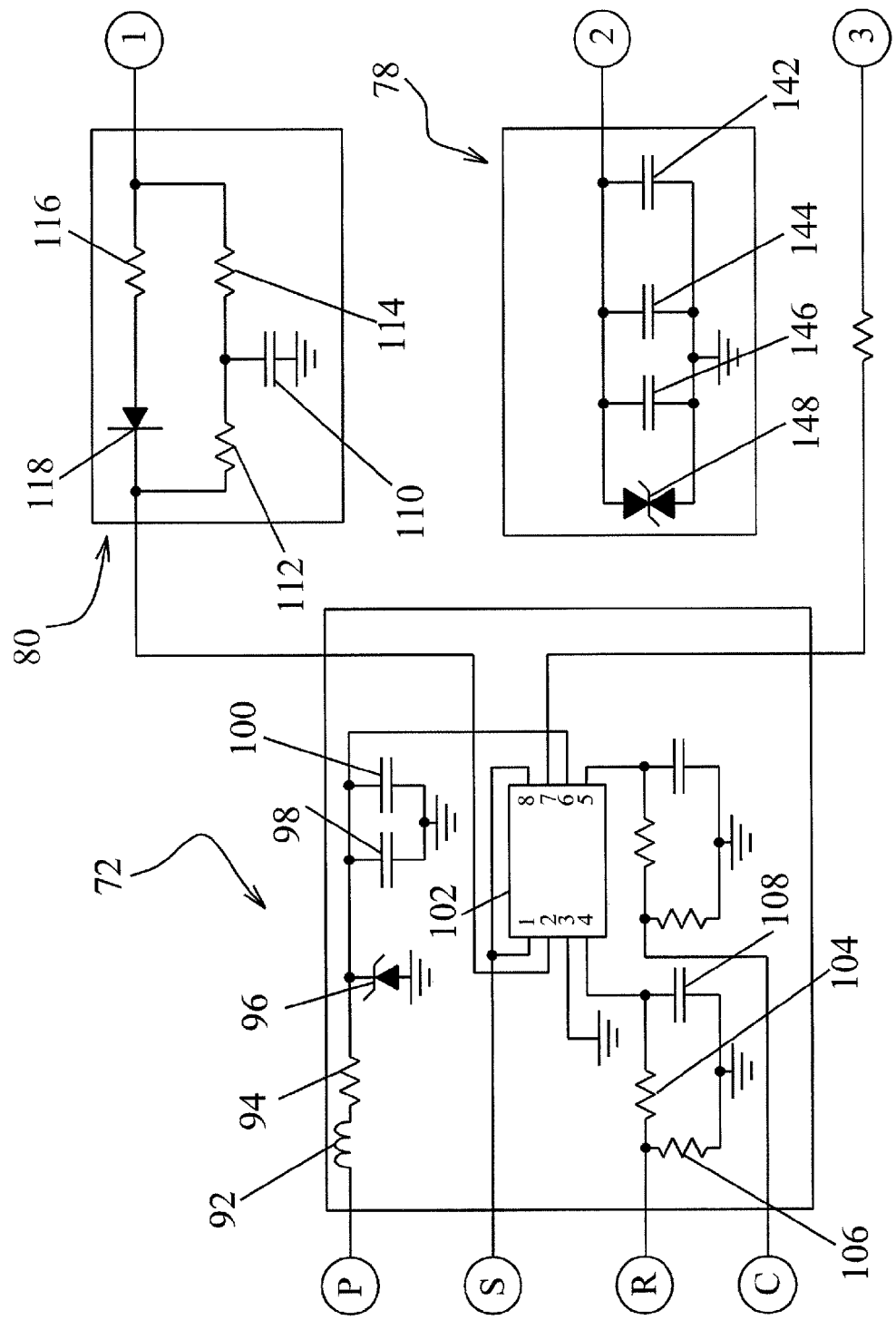
Figure 4B:
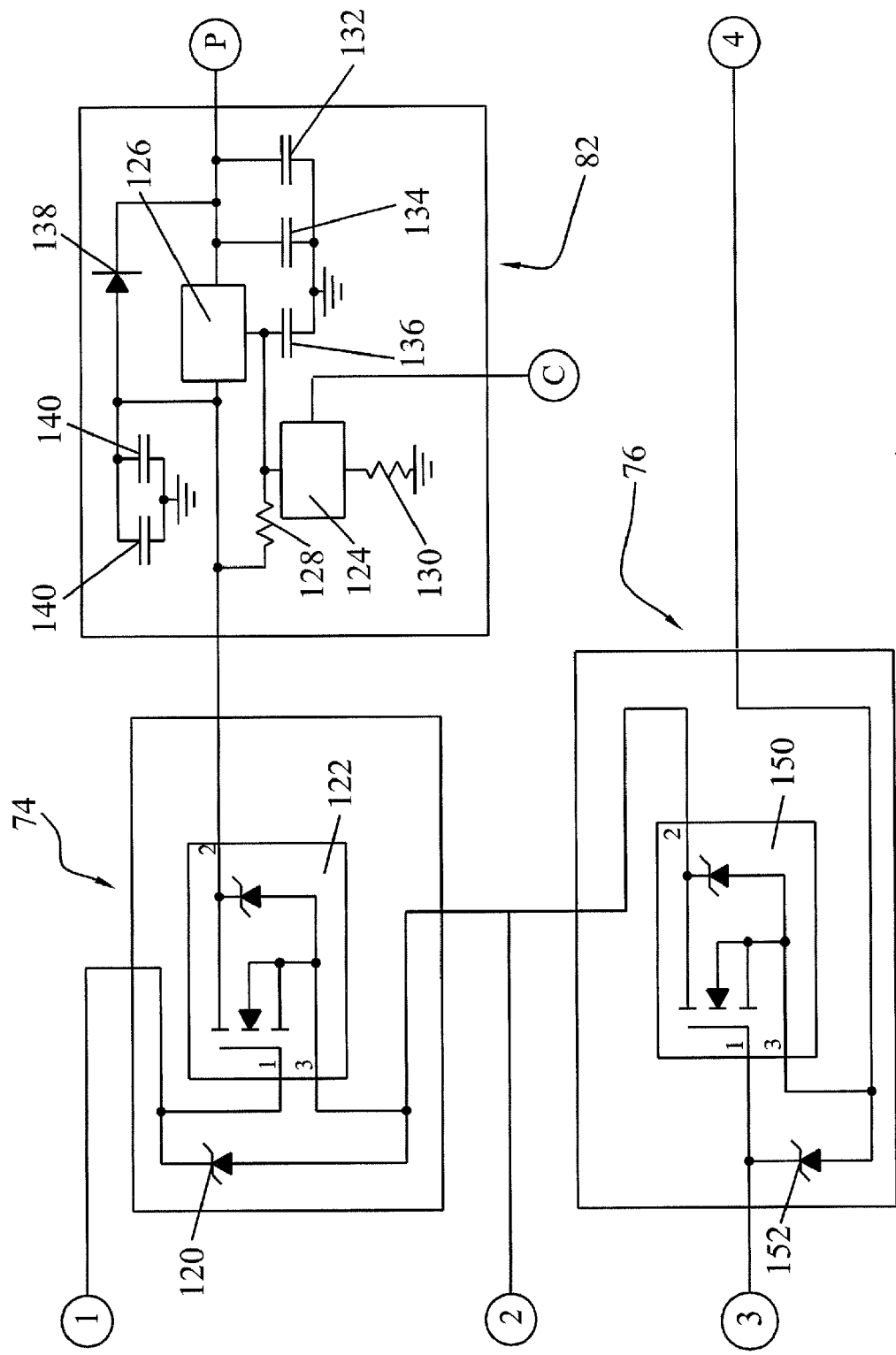
Figure 4C:
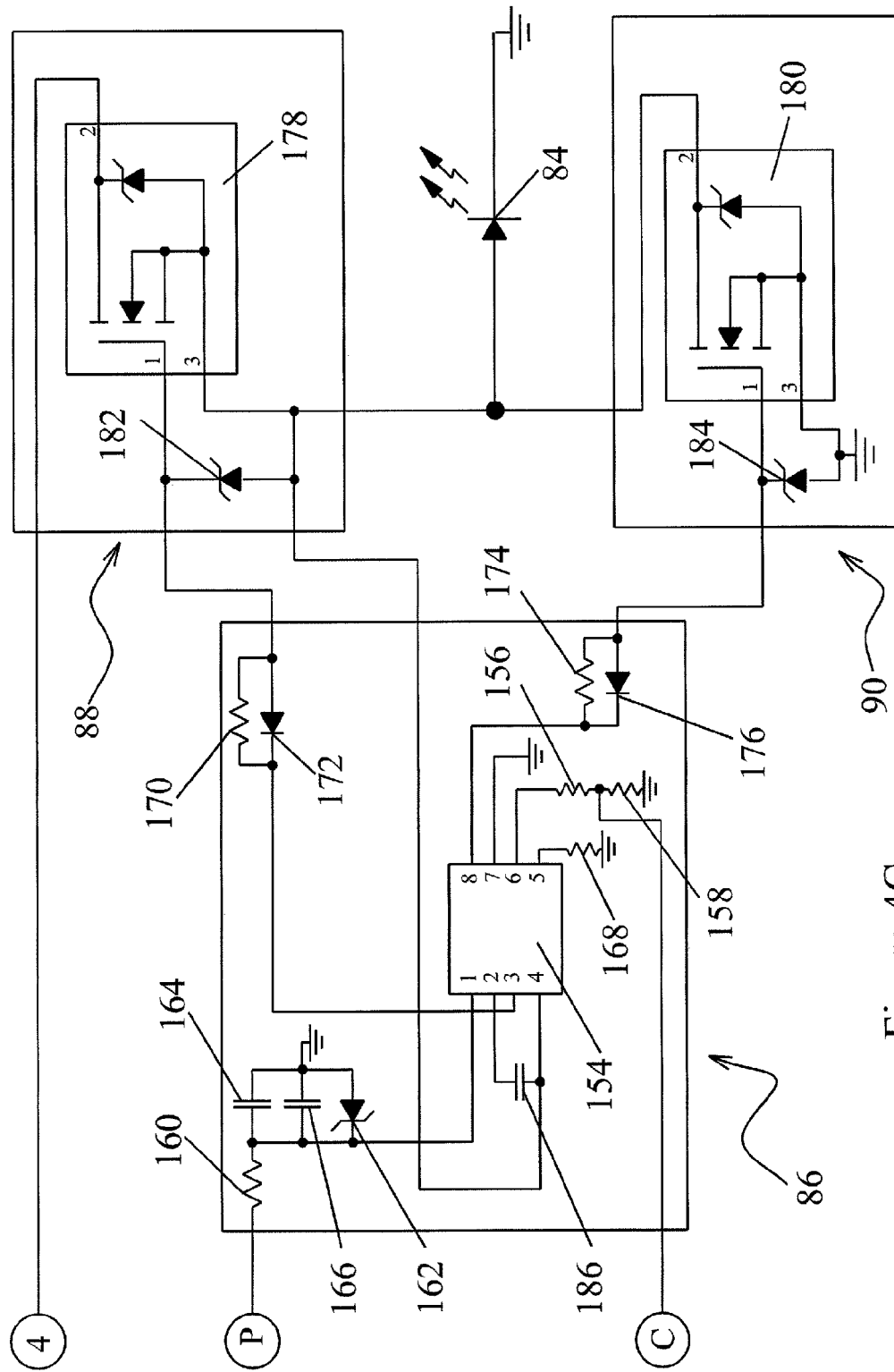

The control circuit 70 is illustrated in greater detail in FIGS. 4A, 4B, and 4C. The switch control unit 72 is connected to a power source at P, preferably 24 V. An inductor 92 provides reverse filtering by preventing high frequency transient electrical signals, produced in the control circuit 70 when the LED device 84 is rapidly switched on and off, from propagating back into other parts of the blood processing apparatus. The incoming voltage is regulated through a resistor 94 and across a Zener diode 96 and capacitors 98, 100, which are connected to ground. One 98 of the capacitors is large enough to smooth fluctuations in the incoming electrical power, while the other capacitor 100 is about two orders of magnitude smaller and presents a path to ground for the high frequency transients blocked by the inductor 92. The regulated voltage is connected to the Vs pin, pin 6, of an integrated switching circuit 102, for example a dual MOSFET driver LTC1255CS8 available from Linear Technology. Pin numbers correspond to the exemplary LTC1255CS8 device. The ground pin, pin 3, of the integrated switching circuit 102, is connected to system ground. The exemplary switching circuit 102 provides two MOSFET switching channels. Such switching channels could be provided by separate integrated circuits or by discrete components. The drain sense pins, pin 1 and pin 8, are both connected to reset circuitry (not shown). Reset circuitry should provide a signal to reset the switching circuit 102 in response to certain conditions such as inadequate voltage, or initial conditions wherein operational delays are introduced to allow initial transients to settle out. The structure of such reset circuitry is known to those of skill in the art and is dependant on the characteristics of the associated microprocessor, and need not be more fully described here. In the switching circuit 102, the gate drive pins, pin 2 and pin 7, are driven to ground when a switch is to be turned off or they are driven high when a switch is turned on. Persons skilled in the art will recognize, of course, that circuits using opposite polarity may also be used. The input pins, pin 4 and pin 5, of the present example are active high and, in the exemplary LTC1255 integrated circuit, should be held low during the application of power to properly set an internal input latch. Input pin 4 is connected through a voltage divider circuit comprising resistors 104, 106 and capacitor 108. A reset circuit (not shown) at connection R keeps input pin 4 low, and the associated MOSFET closed, when adequate power (e.g., 24 V) is not available for an adequate length of time (e.g., longer than 2 seconds). If adequate power is detected, input pin 4 opens gate drive pin 2, and charging of the control circuit 70 begins. Current flows into the charging rate control circuit 80 where a large resistor 112 and capacitor 110 allow the MOSFET to close in a controlled manner and limit the initial rate of current flowing into the capacitor bank 78. It is desirable to manage this inrush of current flow into the capacitor bank to prevent an abrupt increase or spike in current that could adversely affect other circuits, such as microprocessors or cause power supply or system resetting. A small resistor 114 (about 1/10 of the large resistor 112) is connected in series with the large resistor 112, the capacitor 110 being connected between the two resistors 112, 114. A return current path is provided through a resistor 116 and diode 118, connected in parallel with the above-mentioned large and small resistors 112, 114 and capacitor 110, and is forward biased to discharge the gate of the MOSFET integrated circuit 122 in the first switch circuit 74.

A signal from the charging rate control circuit 80 closes the first switch circuit 74, allowing current to flow from the voltage control circuit 82 to the capacitor bank 78. The first switch circuit 74 comprises a power MOSFET integrated circuit 122, for example, an IRFZ44N MOSFET available from International Rectifier, which acts as a switch. The gate of the MOSFET 122 is coupled to the gate drive pin 2 of the switching circuit 122 through the charging rate control circuit 80. The source of the MOSFET is connected to the capacitor bank 78 and the second switch circuit 76. The drain of the MOSFET 122 is connected to the voltage control circuit 82. A Zener diode 120 connected across the gate and the source clamps the voltage at the gate to 12 volts.

The voltage control circuit 82 receives instructions to set the voltage on the capacitor bank 78 consistent with the voltage requirements of LED devices driven by the circuit 70. LED devices emitting different wavelengths or colors generally require different voltage levels. The voltage for the particular control circuit 70 is selected by microprocessors controlling the blood processing apparatus through connection C connected to a digital potentiometer 124. The potentiometer 124 controls the adjust pin on an adjustable voltage regulator 126, for example an LT1085CT available from Linear Technology, by changing the voltage at a location between a first resistor 128, which is connected to the out pin of the regulator, and the potentiometer 124 in series with a second resistor 130, which is connected to system ground. The in pin of the voltage regulator 126 is connected to the 24-volt power supply P. Capacitors 132, 134, and 136 may filter noise and transients from both the power supply P and the potentiometer 124, providing stability of performance. The out pin of the regulator 126 is connected through the drain of the MOSFET 122 to the capacitor bank 78. The regulated voltage at the out pin is the maximum voltage to which the capacitor bank can be charged. A reverse biased diode 138 may be connected between the out pin of the regulator 126 and the in pin of the regulator to protect the regulator in the event that the capacitor bank is charged, but the connection to the power supply P is interrupted. One or more capacitors 140 may also be connected to the out pin of the regulator whereby high frequency transient voltages may be conducted to ground.

The capacitor bank 78 comprises one or more capacitors 142, 144, 146 connected on one side between the first switch circuit 74 and the second switch circuit 76 and on the other side to system ground. A bidirectional transient voltage suppressor or "back-to-back" Zener diode 148 may be provided in parallel with the capacitors to provide transient protection for the capacitors, particularly if the rated voltage of the capacitors is close to the maximum voltage available from the power supply. Physically smaller capacitors are desirable due to constraints of space in the preferred application. When the first switch circuit 74 is closed, the capacitors 142, 144, 146 are charged to the voltage set by the voltage control circuit 82. When the second switch circuit 76 is closed, the capacitors 142, 144, 146 are connected to further circuit elements and are ready to provide drive current to the LED device, as more fully explained below.

The second switch circuit 76 comprises a power MOSFET integrated circuit 150, for example, an IRFZ44N MOSFET available from International Rectifier, which acts as a switch. The gate of the MOSFET 150 is coupled to gate drive pin 7 of the switching circuit 102 in the switch control unit 72. The drain of the MOSFET is connected to the capacitor bank 78 and the first switch circuit 74. The source of the MOSFET 150 is connected through the first rapid response switch 88 to the LED device 84. A Zener diode 152 connected across the gate and the source clamps the voltage at the gate to 12 volts.

Electric power delivered from the capacitor bank 78 through the second switch circuit 76 to the LED device 84, as connected through first rapid response switch 88, is controlled by the pulse drive controller 86, which selectively opens and closes the first rapid response switch 88 and the second rapid response switch 90, allowing current to flow into and out of LED device 84. The pulse drive controller 86 comprises a half-bridge gate driver 154, such as an LM5104 integrated circuit from National Semiconductor. The gate driver 154 receives signals from the microcomputer C at an input pin 6. A resistor 156 in series with the computer input and the input pin 6 limits the current at the pin. Another resister 158 connected to the computer input and to system ground holds the voltage at the input pin 6 low in the absence of a control pulse from the computer. The VDD or voltage in pin 1 of the gate driver 154 receives electrical power for the gate driver through a voltage regulator comprising a resistor 160 and 12-volt Zener diode 162 connected in series between the power supply P and system ground. One or more capacitors 164, 166 may be connected in parallel with the Zener diode to conduct high frequency transients to ground. The gate driver is grounded through Vss pin 7. A resistor 168 connecting the dead time programming pin 5 to system ground sets a delay between high and low transitions in the gate driver. This delay prevents the gate driver from closing the first rapid response switch 88 and the second rapid response switch at the same time, which would short the capacitor bank to ground. In response to a signal from the computer C, the gate driver 154 produces a signal at high out pin 3. The signal passes through a resistor 170, which damps the turn-on characteristics of the first rapid response switch 88 and controls voltage spikes and generation of radiated electrical interference as the first rapid response switch is closed. The gate of MOSFET 88 may discharge through diode 172 in parallel with resistor 170. As the signal from the computer C ends, the gate driver 154 produces a signal at low out pin 8. This signal also passes through a resistor 174, which damps the turn-on characteristics of the second rapid response switch 90 and controls voltage spikes and generation of radiated electrical interference as the second rapid response switch is closed. The gate of MOSFET 180 may discharge through diode 176 in parallel with resistor 174. The second rapid response switch 90 is normally "on" or "closed", except when a pulse is produced. In contrast, first rapid response switch 88 is normally "off" or "open". Thus, in the exemplary embodiment, when the signal from a microprocessor through C is low, switch 88 is off, while switch 90 is on, and the LED device 84 produces no light. As the signal from the microprocessor through C goes high, both switches 88, 90 are momentarily open or off. As the output at C remains high, switch 88 turns on (closes), while switch 90 stays open or off. The LED device produces light. As the signal from the microprocessor returns to low, both switches 88, 90 are again momentarily open or off. Switch 90 then turns on or closes, and the LED device discharges to ground. One skilled in the art will recognize that the polarity of the signals, the states of the switches, and the direction of current flow through the LED device could be reversed without departing from the teachings of the present invention.

Both the first rapid response switch 88 and the second rapid response switch 90 are comprised of a power MOSFET 178, 180, for example an IRFZ44N MOSFET available from International Rectifier, with a Zener diode 182, 184 connected across the gate and the source of the respective power MOSFET as a voltage clamp for the respective gate of the MOSFET 178, 180. The drain of the MOSFET 178 of the first rapid response switch 88 is connected to the second switch circuit 76, as described above. When the capacitor bank is charged and the second switch circuit 76 is closed, the signal to the gate of the MOSFET 178 from the gate driver 154 causes the MOSFET 178 to conduct power from the MOSFET source through the LED device 84 to ground. The MOSFET source is also connected to a high side MOSFET source connection pin 4 on the gate driver 154. A bootstrap capacitor 186 connects the source connection pin 4 to a bootstrap rail pin 2 of the gate driver 154. When the signal from the computer C ends, the gate driver 154 initially both opens the rapid response switch 88 and leaves the second response switch 90 open for a very brief time (on the order of nanoseconds, as adaptively controlled by gate driver 154), thereby preventing a short circuit from the capacitor bank to system ground. The gate driver 154 then provides a signal to the gate of the MOSFET 180 in the second rapid response switch 90, causing the MOSFET 180 to conduct to system ground. Any power energizing the LED device 84 is conducted away from the LED device to ground. A sharp, well-controlled square-wave voltage, with well-defined leading and trailing edges, can thereby be produced on the LED device, so that the duration and magnitude of illuminations produced by the LED device are consistent.

Preferably, each control circuit 70 controls an LED device or devices of a single type or output frequency. The LED device may produce illumination in the visible or invisible regions of the spectrum, such as red, green or infrared light or full-spectrum white light, as may be appropriate for the desired application. Preferably, multiple LED devices may be connected in parallel, reducing the cost, size and complexity of the drive circuits. In addition, failure of one of the LED devices would not completely incapacitate a specific control circuit.

Figure 5:
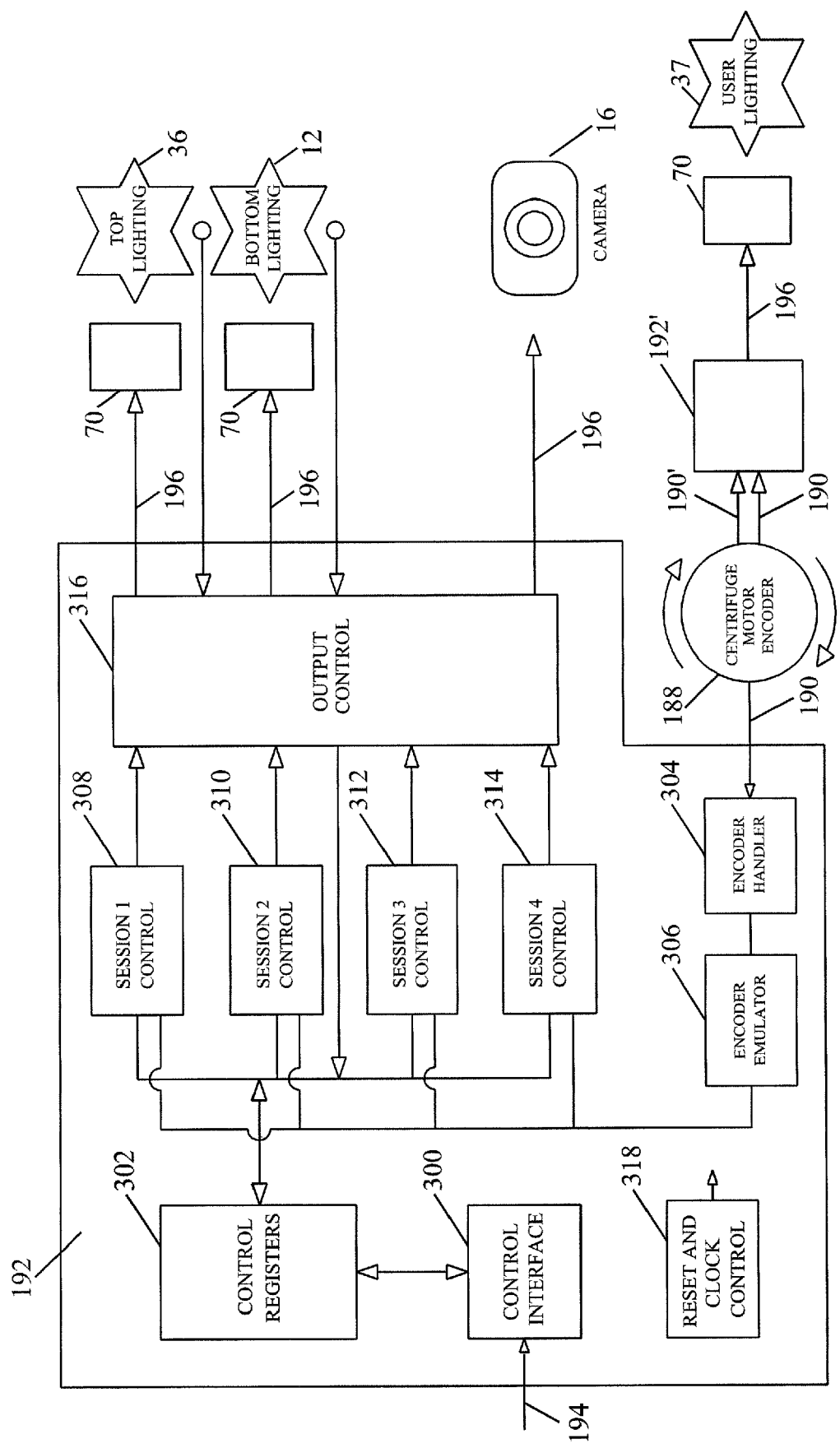
FIG. 5 shows a functional flow diagram representing a method and apparatus for synchronizing light pulses generated by top and bottom pulsed LED light sources trigger and trigger delay settings.
Figure 7:
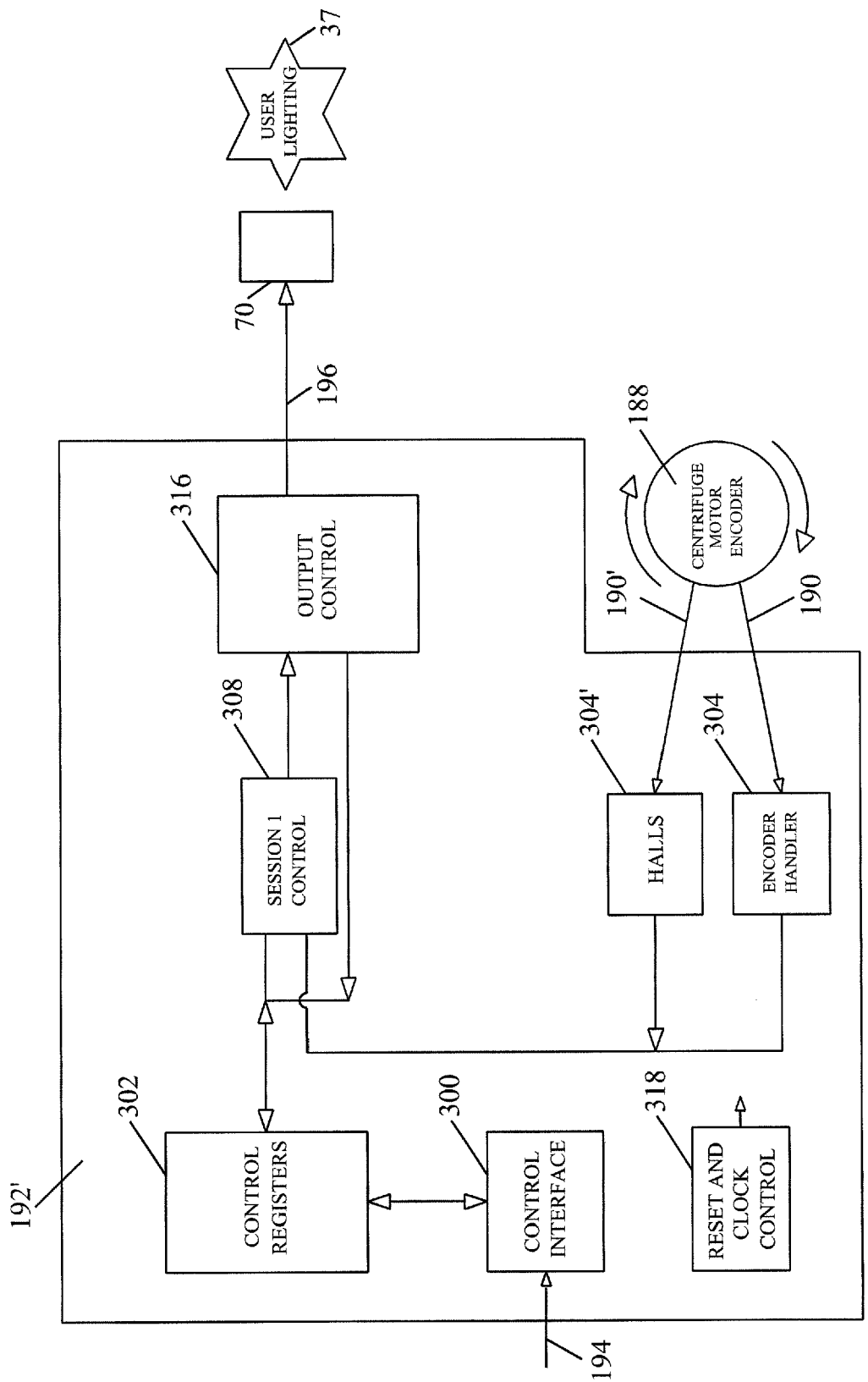
FIG. 7 shows a functional flow diagram for synchronizing light pulses generated by a user strobe LED light sources with both encoder and Halls effect position sensors.

FIG. 5 shows a functional flow diagram representing a method of synchronizing light pulses generated by top and bottom pulsed LED light sources and camera shutter and gate settings. Similar, independent circuitry controls user observation pulsed LED light sources, as shown in FIG. 7. Independent circuits provide back-up security should the automatic controls described in connection with FIG. 5 fail. The user light source allows manual or operator control of the interface, as is known in the art. As illustrated in FIG. 5, encoded motor system 188 generates one or more output signals 190 corresponding to the rotational position of the optical cell. Output signals 190 are received as input to the synchronization and timing controller 192. Synchronization and timing controller 192 is also configured to receive control signals 194 from a device controller. Control signals 194 and output signals 190 are processed by synchronization and timing controller 192, and serve as the basis of a plurality of trigger signals 196 which are sent to the top pulsed LED light source, the bottom pulsed LED light source and the CCD camera. Optionally, one or more trigger signals may also be used to adjust the lighting in the centrifuge chamber to allow a user to visually assess the state of the centrifuge during processing, preferably using the independent circuit of FIG. 7. An advantage of this aspect of the present invention is that timing and synchronization of light pulses and camera settings are handled by the synchronization and timing controller 192 without expenditure of other system resources, such as processing time of the device controller.

Use of LED light sources in the present invention is beneficial because these light sources are small, light weight and have relatively low power consumptions compared to many conventional non-LED light sources. LED light sources also exhibit long operating lifetimes, high efficiency and uniform intensity with little generated heat. In addition, LED light sources are capable of pulse operation generating discrete pulse having accurately selectable temporal characteristics such as pulse width and initiation time. Pulse LED sources also are capable of generating pulses having substantially uniform intensities and wavelength distributions. Use of LED is also preferred for some applications of the present invention because it provides good control of the wavelength distribution of the upper and/or lower illumination beams. The present invention includes embodiments, wherein the wavelength distribution of top and bottom illumination beams is selectively adjustable by mixing the output of LEDs having different colors, such as red, green and white LEDs and independently controlling the duration of illuminations of the different colors or wavelengths. In these embodiments, the wavelength distributions of top and bottom illumination beams may be independently selected on a shot per shot basis to optimize a desired optical measurement, such as the measurement of the position of phase boundaries between optically differentiable blood components and/or the compositions of extracted blood components passing through an extraction port.

The synchronization and timing controller 192 ("STC") comprises independent circuitry that monitors the filler rotation and controls the lights and the camera in response to parameters received from the computer, thereby allowing the computer to be dedicated to other data processing. Concentrating the timing and synchronization required for acquiring images allows high-speed images to be made while reserving the device microcomputer for image processing, for example. Preferably, the synchronization and timing controller is implemented in dedicated circuitry. More preferably, the STC 192 comprises an FPGA such as a ProASIC Plus™ flash FPGA (Field Programmable Gate Array) available from Actel programmed with a hardware description language such as Verilog.

The STC 192 has two main functions. First, it locates and triggers the start of "sessions" throughout the rotation of the filler. Secondly, the STC controls the timing for the pulse outputs needed during a session to activate such elements as the camera shutter, top strobe light or lights, bottom strobe light or lights, or a user strobe light 37 (FIG. 5). The STC has the capability of triggering any combination of the camera, top strobe lights, bottom strobe lights or user strobe light at multiple times, representing multiple locations around the circumference of the filler.

Synchronization of a session to the rotation of the filler is accomplished by monitoring the output of a motor encoder hard mounted to the centrifuge motor and allowing software to select at what point on the rotation to trigger a session to start. It is desired that the apparatus will be provide a plurality of session triggers, preferably two or more session triggers in a rotation of the filler. With at least two sessions available, the system could image at different locations or use different sessions to hold different settings, allowing the device controller 40 to select between settings without full reprogramming of parameters.

The timing of the pulses to activate the camera shutter, top strobe light, and bottom strobe light within a triggered session may be accomplished with high precision timers that can be loaded by software from a control computer. Preferably, the STC will have a single FPGA for the logic circuits required and very minimal external circuitry such as a clock oscillator and reset pull-up. A session trigger synchronizes the start of lighting or image acquisition with absolute positions of the filler. The STC shall provide the ability for software to select a reference point with respect to the rotation of the filler to trigger the beginning of a camera image acquisition session or other lighting event ("session trigger"). The session trigger accuracy is preferably better than 0.1 degrees of filler rotation. The centrifuge motor (controlling the rotation of the filler) has at least a basic A/B encoder that provides an absolute reference pulse once per revolution and preferably a minimum of 2048 pulses per revolution of the motor. The centrifuge motor is coupled to the filler through a 2-to-1-reduction drive train, that is, the motor spins half the speed of the filler. With a 2048 pulse encoder (1024 pulses per rotation of the filler implies 4096 pulses per rotation using quadrature), the session trigger accuracy should be 360/4096 or 0.088 degrees of filler rotation. The STC provides the ability for software to calibrate the zero position of the rotation to be anywhere (within the accuracy previously specified) along the rotation of the filler. The software-driven computer calibrates the session trigger position to 0 and then visually seeks for the filler zero desired by changing the zero position calibration setting. With this set, the control computer has mathematical models of the filler to know positions of areas of interest from that calibration point. The STC monitors the instantaneous speed of the filler at least every rotation of the motor to allow for functional decisions by the related to RPM. This RPM does not need to be reported to the control computer. The STC allows the control computer to manually select for a session to trigger once per rotation of the filler (1× Mode) or once for every other rotation of the filler (½× Mode). The control computer selects an RPM above, which the hardware will shift from 1× mode to ½× mode automatically for each session. A manual ½× mode setting overrides the automatic change to ½× function.

Figure 6A:
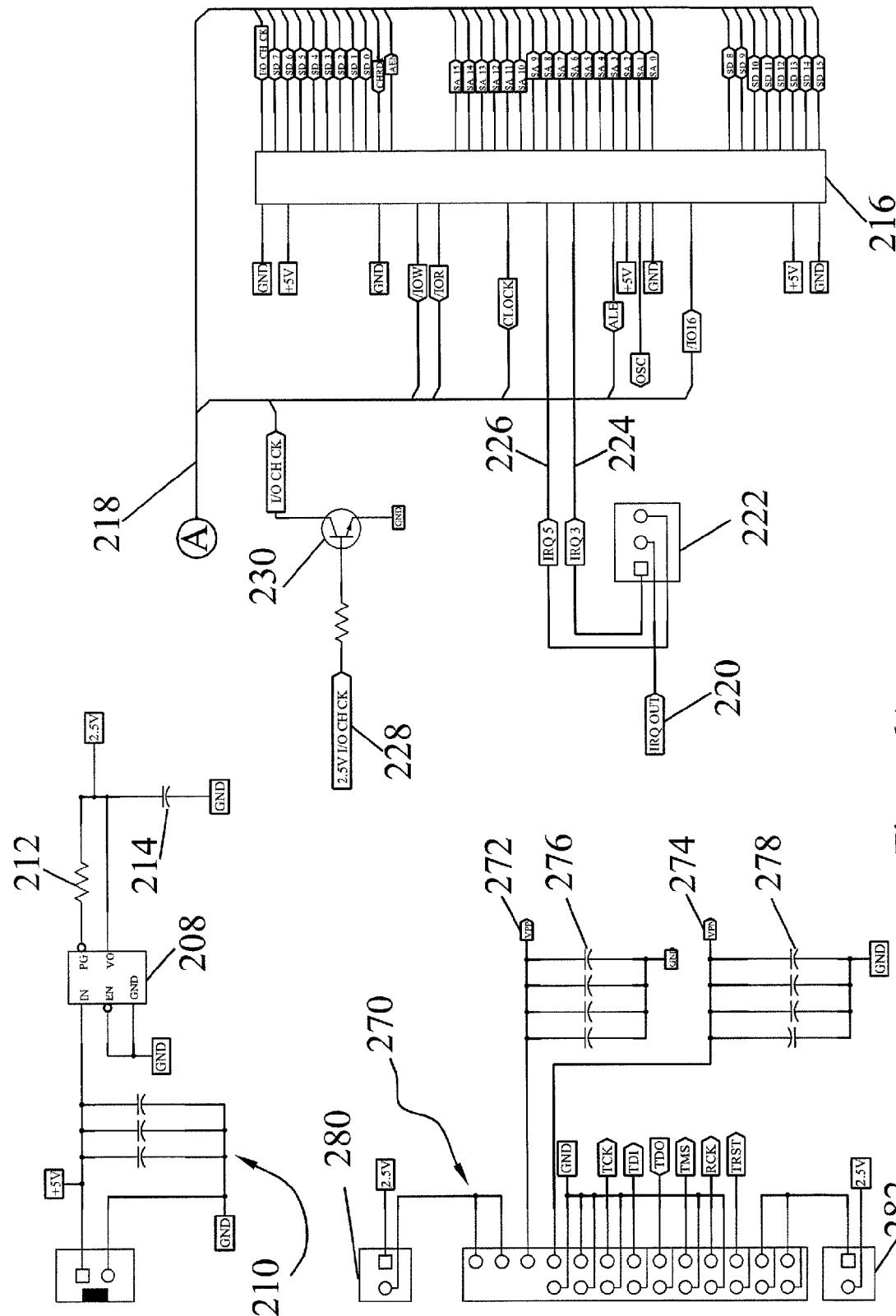
FIGS. 6A, 6B, 6C and 6D are schematic diagrams of a circuit for a synchronous timing controller (STC) according to the present invention.
Figure 6B:
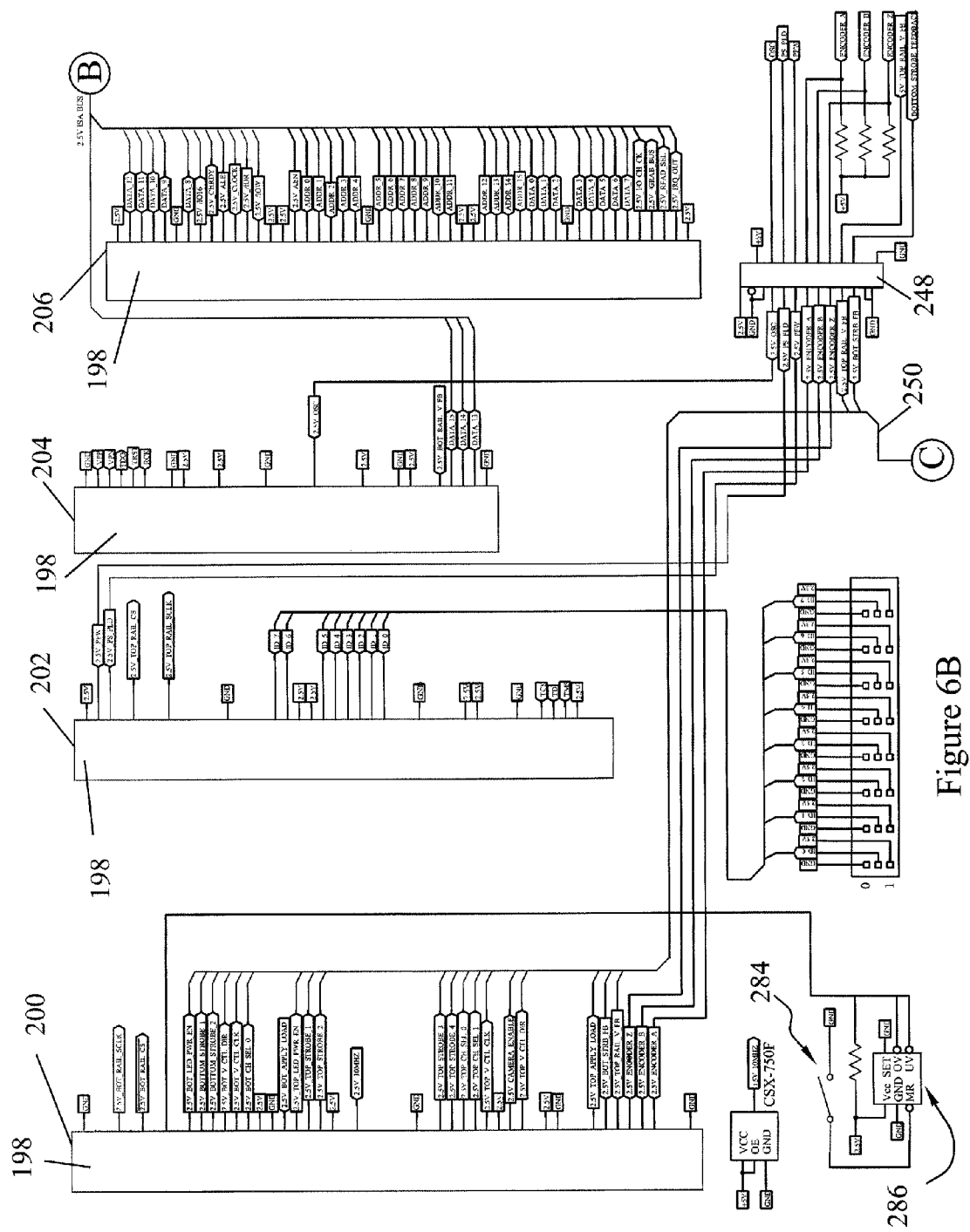
Figure 6C:
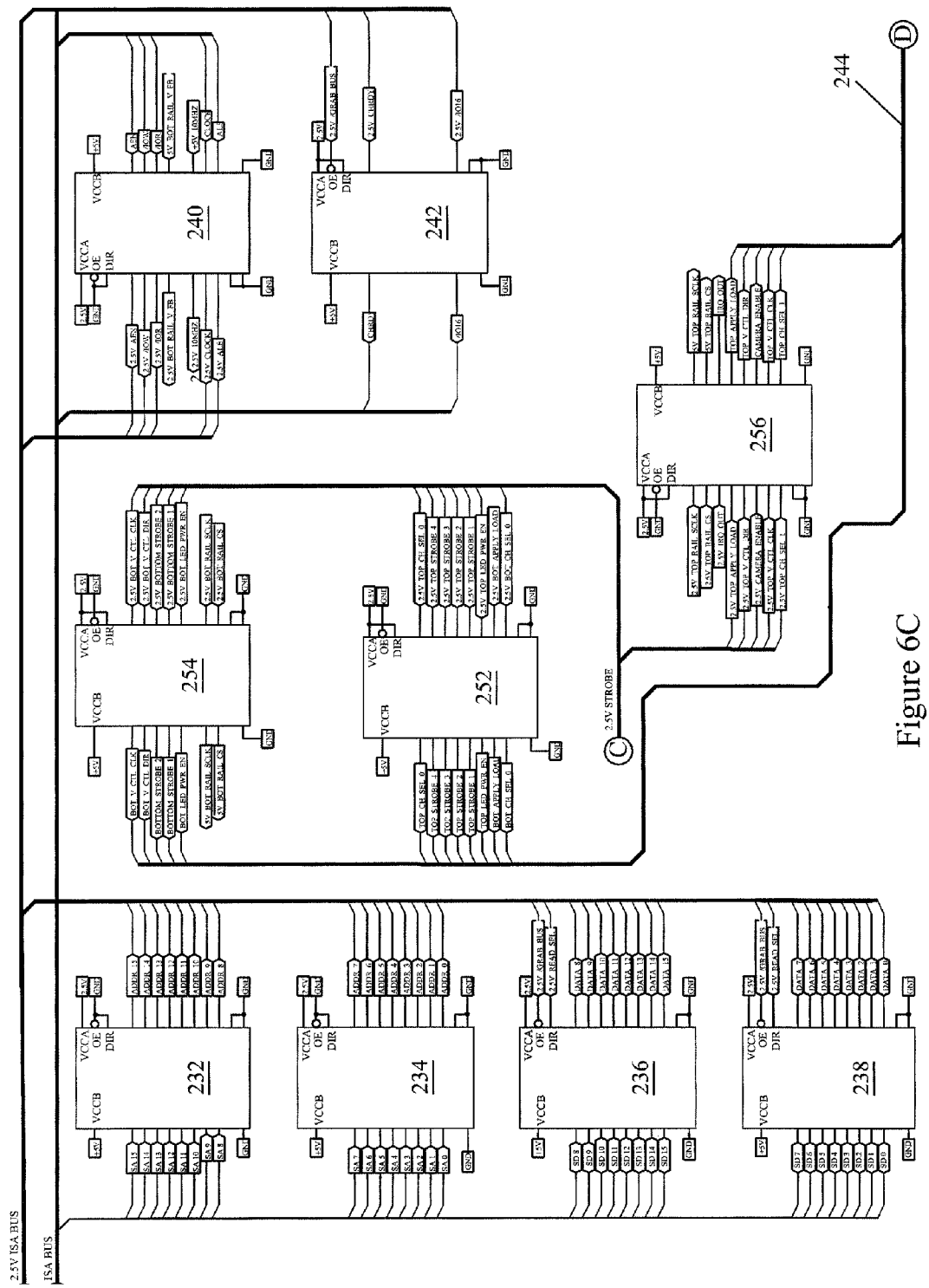
Figure 6D:
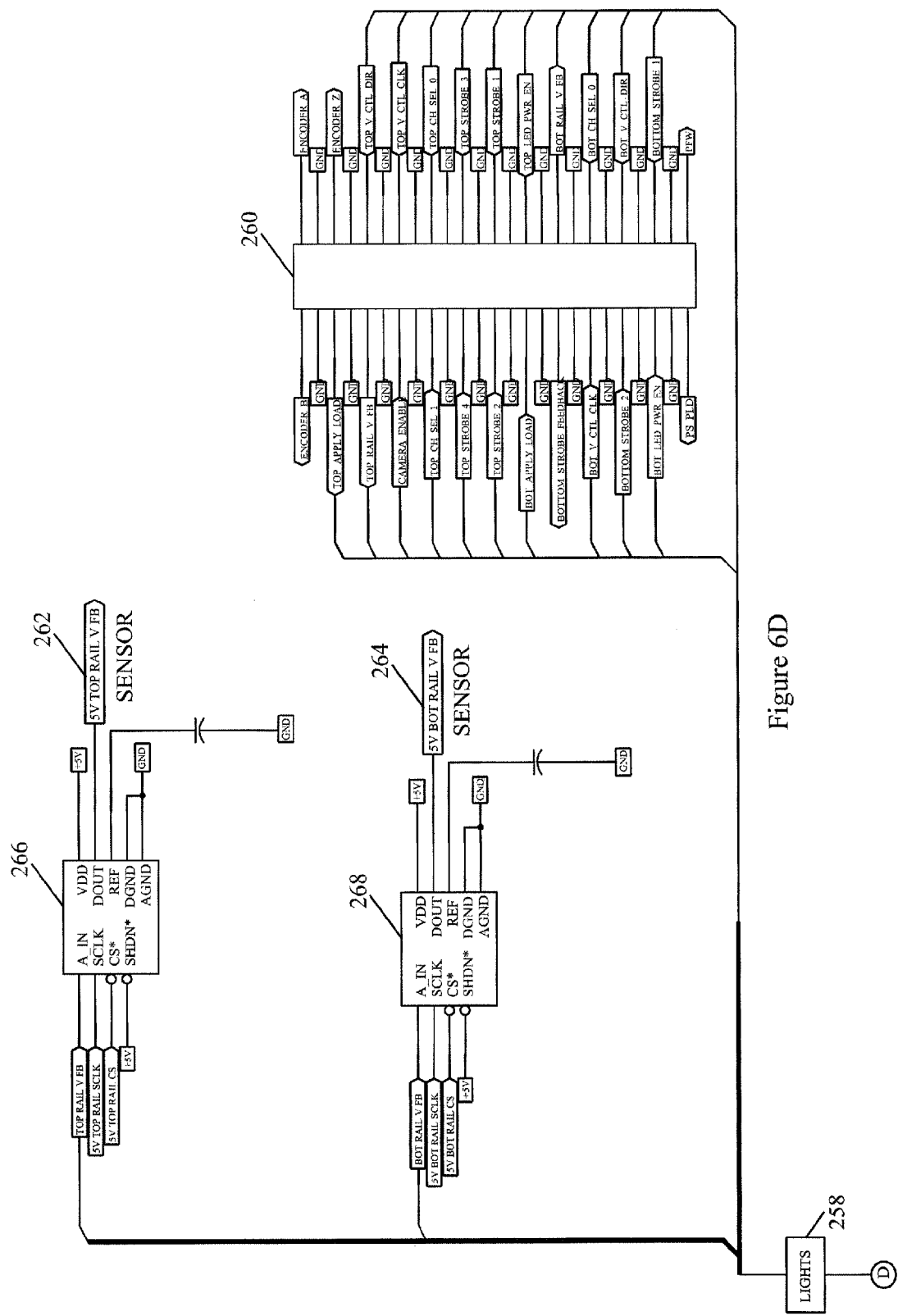

The functional concepts of the STC have been illustrated and described above in connection with FIG. 5. More detail of the circuit structure is illustrated in FIGS. 6A, 6B, 6C and 6D. In the illustrated embodiment, an FPGA circuit 198 such as a ProASIC Plus (trademark) flash FPGA (Field Programmable Gate Array) available from Actel provides a programmable circuit structure for the digital circuit implementing the functions needed for control of the camera and lights in this apparatus. In FIG. 6B, the four edges 200, 202, 204, and 206 of the single FPGA circuit 198 are shown separately in exploded fashion for clarity. In the illustrated embodiment, the operating voltage of the FPGA circuit 198 is 2.5V, compared to the preferred 5V operating voltage for other components of the blood processing system. A voltage converter 208, with input filter capacitors 210 and output resistive load 212 and output filter capacitor 214, provides the required voltage. A 5V bus 216 couples the STC circuit to the control computer (not shown in FIG. 6A). The control computer communicates parameter commands through the 5V bus 216 to set the various sessions for the lights and the camera and receives signals reporting the functioning of the STC circuit. The 5V bus provides an ISA communication bus 218 which couple the other components of the STC circuit. An interrupt signal 220 may also be provided through a jumper 222 to selectable interrupt lines 224, 226. A 2.5V channel check signal 228 is coupled through a buffering transistor 230 for an input-output check at 5V. Signals on the 5V ISA bus 218 are connected through a plurality of level shifters 232, 234, 236, 238, 240 and 242 to a 2.5V ISA bus 244, which is coupled to the FPGA circuit 198. The FPGA circuit 198 also receives encoder signals from an encoder 246 coupled to the centrifuge motor and the filler. A level shifter 248 translates the 5V signals produced by the encoder 246 to 2.5V signals for processing by the FPGA circuit 198. The FPGA circuit 198 produces strobe control signals on a 2.5V strobe line 250. The strobe line connects to the top lighting 36 through a top lighting voltage shifter 252; to the bottom lighting 12 through a bottom lighting shifter 254; and to the camera through a camera voltage shifter 256. A Lights line 258 connects to the ISA bus and has an auxiliary coupling 260 for physical connection of the STC circuit 198 to other components. In addition a top light sensor 262 and a bottom light sensor 264 may be coupled through interface circuits 266, 268 to the FPGA circuit 198. These sensors may be used to provide positive feedback of applied light pulses.

As will be explained further below, the circuitry of the FPGA circuit 198 is set through application of a programmable circuit design using, for instance, Verilog (trademark) hardware description language. The STC circuit 192, therefore, may have a re-programming port 270 for receiving commands that would reconfigure the logical structure of the FPGA circuit 198. The re-programming port 270 may have voltage connections 272, 274 with filters 276, 278, for matching programming voltage levels when the re-programming port is connected to an external computer for transmission of reconfiguration commands. The reprogramming port 270 may be locked by jumpers 280, 282 to 2.5V levels to prevent inadvertent alteration of the FPGA circuit 198.

Finally, both a manual reset 284 and a circuit-controlled reset 286 may be provided to return the STC circuit 192 to an initial state. The circuit-controlled reset 286 is usually responsive to the control computer and may be activated in response to a detected error condition. Similarly, the manual reset 284 may be used by an operator to restart the STC circuit, should the need arise.

The configuration of the FPGA 198 will be explained in view of a Verilog hardware description language application. Clearly, other hardware description languages could be used, or the circuits could be statically designed as a single custom array of logic elements or other circuit components. One skilled in the art would recognize such alternatives to the disclosed embodiment.

Control Interface and Control Register

A control interface 300 is used to access the registers for calibration, setting triggers, and configuring session flows. Preferably, all registers are memory-mapped locations on the ISA interface, but a USB digital I/O board may also be used for the interface implementation. The STC 192 may provide a control interface designed for use with a 24 bit digital I/O board including handshake (acknowledge). The control interface 300 allows read/write to the registers of the STC 192 for setting parameters and reviewing status. No individual status or input lines are required outside the 24-bit interface. The control interface 300 allows the controller to write to or read from applicable registers at any time throughout the rotation of the filler. The control interface may have a "busy time" during which time reads and writes on the interface are not allowed. The busy time should coincide with the time when a session is running. During the control interface busy time any reads or writes to the interface may be delayed (acknowledge will not go high) until the busy time expires. In this way, no write or read commands and information will be lost no matter when the commands are issued. During the busy time the current contents of the registers is used to set up timers, session triggers and calibration for the next rotation of the filler. The control interface 300 for the STC uses an ISA bus. For reliable communication, a failing edge of a "bus address latch enable" ("bale") indicates an instruction or address has been stable 60 ns and is deemed a valid signal. Chip select is latched. Address decode logic set forth below can decode in less than 30 ns. Chip select is reset if the signal is high on a new bale high. Hereinafter, exemplary Verilog code is set forth, illustrating the logical structure for functional digital circuitry. Exemplary code is indented. Explanatory comments will begin at the left margin.

In many of the logically described circuits disclosed herein, a square wave signal is produced, commencing at a first condition and terminating at a second condition. The signal may also be terminated in response to a reset signal. The interface control circuit 300 begins to check for addresses on the ISA bus when it receives a negative edge on the "bale" signal and ends checking when a positive edge of the cycle done signal is received. The process may be interrupted is a negative edge on the reset signal is received. The interface control circuit 300 sets a chip select flag to false if either reset is false or cycle done is true. Otherwise, the interface control circuit 300 checks if an address received from the ISA bus is within an acceptable range and sets the chip select flag to true. If the address is out of range, the chip select flag is set to false.

```
always @(negedge bale or negedge reset_n or posedge cycle_done)
begin
    if(reset_n == 1'b0 || cycle_done == 1'b1)
        chip_select <= 1'b0;
    else begin
        if((sa >= base_addr) && (sa <= base_addr+ADDR_SPACE_SIZE-2) && (aen == 1'b0))
            chip_select <= 1'b1;
        else
            chip_select <= 1'b0;
    end
end
```

The interface control 300 filters for incoming iowc_n (input-output write command, active low) and iorc_n (input-output read command, active low) and combines the two signals into a single combined command flag.

```
always @(iorc_n or iowc_n) begin
    if(iorc_n == 1'b0 || iowc_n == 1'b0)
        comb_command = 1'b0;
    else
        comb_command = 1'b1;
end
```

The interface control circuit 300 filters for ringing on a low going edge. This feature is only active when chip select flag is active or true. The circuit 300 checks for the existence of a combined command (either a read or a write signal from the computer control) a positive bus clock signal after a false or low condition of the combined command or a reset signal. If reset_n signal is active (high) and there was a bus clock signal, a flag indicating that the combined command went low is set to false, that is, a read or write command is not being received from the control computer. Otherwise, if chip select is true, meaning that the address is within a valid range, a "command went low" flag is set to true, indicating that a read or write is being attempted. To synchronize the interface control circuit 300 with the bus clock, a flag "bus clock positive after combined command low" is set true or false, depending on conditions of the bus clock, whether a valid address in the chip has been selected, or if a reset condition exists.

```
always @(negedge comb_command or posedge
bclk_pos_after_command_low or
negedge reset_n) begin
    if(reset_n == 1'b0 || bclk_pos_after_command_low == 1'b1)
        command_went_low <= 1'b0;
    else begin
        if(chip_select == 1'b1)
            command_went_low <= 1'b1;
    end
```

-continued

```
end
always @(posedge bclk or negedge chip_select or negedge reset_n)
begin
    if(reset_n == 1'b0 || chip_select == 1'b0)
        bclk_pos_after_command_low <= 1'b0;
    else begin
        if(command_went_low == 1'b1)
            bclk_pos_after_command_low <= 1'b1;
    end
end
```

Next, the interface control circuit 300 filters for ringing on a high-going edge, if the above-described low-going filter has been activated first. The combined command must remain high for a selected time, that is, a number of cycles of the bus clock, for the signal change to be considered a valid signal, as shown in the following logic statements.

```
always @(posedge comb_command or posedge
bclk_neg_after_command_high or
negedge reset_n) begin
    if(reset_n == 1'b0 || bclk_neg_after_command_high == 1'b1)
        command_went_high <= 1'b0;
    else begin
        if(bclk_pos_after_command_low == 1'b1)
            command_went_high <= 1'b1;
    end
end
always @(negedge bclk or negedge chip_select or negedge reset_n)
begin
    if(reset_n == 1'b0 || chip_select == 1'b0)
        bclk_neg_after_command_high <= 1'b0;
    else begin
        if(command_went_high == 1'b1)
            bclk_neg_after_command_high <= 1'b1;
        else
            bclk_neg_after_command_high <= 1'b0;
    end
end
```

A command active flag is set true if there is a valid read or write condition, as determined by the above tests.

```
always @(posedge command_went_low or posedge
command_went_high or negedge reset_n) begin
    if(reset_n == 1'b0 || command_went_high == 1'b1)
        command_active <= 1'b0;
    else
        command_active <= 1'b1;
end
```

The command active flag is considered valid only if the chip_select is also true. A "chip select gated" flag is set true if both conditions are met.

```
always @(chip_select or command_active) begin
    chip_select_gated = chip_select & command_active;
end
```

A signal is then sent to the level shifters and tri-state circuits 232, 234, 236, 238, and 248 to respond to signals or "grab" the ISA bus when the chip select gated flag is set true. This permits a read or write signal to be received from the control computer. The bus is released when a "cycle done" condition is detected.

```
assign grab_bus_n=~chip_select_gated;
```

A cycle is deemed done if chip_select is active and there has been a timeout since chip_select went high or the next bus clock falling edge after command_active goes false while selected (cycle_end_count==1'b0)

```
always @(timeout_trig or cycle_end_count or chip_select) begin
    if((timeout_trig == 1'b1 || cycle_end_count == 1'b0) &&
        chip_select == 1'b1)
        cycle_end_trig = 1'b1;
    else
        cycle_end_trig = 1'b0;
end
always @(posedge cycle_end_trig or negedge reset_n or negedge
chip_select) begin
    if(reset_n == 1'b0 || chip_select == 1'b0)
        cycle_done <= 1'b0;
    else
        cycle_done <= 1'b1;
end
```

The cycle timeout, that is the maximum permitted duration of a cycle, is set to a value CYCLE_TIMEOUT_BCLKS (cycle timeout for bus clocks) by a command from the control computer to the CYCLE_TIMEOUT_BCLKS variable. All capital letters are used hereinafter for constants or for parameters whose value is set by the control computer. Such values are treated as operating constants by the STC circuit 190. After chip_select goes high or true, the following circuit logic decrements a cycle_timeout_count from the CYCLE_TIMEOUT_BCLKS value until zero time is reached. Thereafter, a timeout trigger is set to true if time for the cycle has expired. This may be considered as a recovery or reset from an error condition.

```
always @(negedge bclk or negedge reset_n) begin
    if(reset_n == 1'b0)
        cycle_timeout_count <= CYCLE_TIMEOUT_BCLKS;
    else begin
        if(cycle_timeout_count > 18'd0 && chip_select == 1'b1)
            cycle_timeout_count <= cycle_timeout_count-1;
        else
            cycle_timeout_count <= CYCLE_TIMEOUT_BCLKS;
    end
end
always @(posedge bclk or negedge reset_n) begin
    if(reset_n == 1'b0)
        timeout_trig <= 1'b0;
    else begin
        if(cycle_timeout_count == 18'd0)
            timeout_trig <= 1'b1;
        else
            timeout_trig <= 1'b0;
    end
end
```

A cycle end is signaled by the next bus clock signal (bclk) failing edge after the command_active flag is set to false, that is, the next bus clock falling edge after chip_select_gated goes low. When the end of a cycle is detected, the circuit performs several housekeeping operations, preparatory to the commencement of a new cycle. For example, the variable cycle_end_count will be set to either 1 (true) or 0 (false). This may be considered as an expected recovery or reset, that is, a condition expected in the normal course of operation.

```
always @(negedge chip_select_gated or negedge reset_n or negedge
chip_select) begin
    if(reset_n == 1'b0 || chip_select == 1'b0)
        cs_gated_went_low <= 1'b0;
    else
        cs_gated_went_low <= 1'b1;
end
always @(negedge bclk or negedge reset_n or negedge chip_select)
begin
    if(reset_n == 1'b0 || chip_select == 1'b0)
        cycle_end_count <= 1'b1;
    else begin
        if(cycle_end_count > 1'b0 && chip_select == 1'b1 &&
cs_gated_went_low == 1'b1)
            cycle_end_count <= 1'b0;
        else
            cycle_end_count <= 1'b1;
    end
end
```

The ISA bus carries a signal CHCHK# that is intended to allow ISA expansion boards to signal an error to a host computer. In most systems, this signal going low causes a non-maskable interrupt to be sent to the host computer. On the STC circuit, this signal is driven low as soon as an ISA bus transaction is started, but is not completed for about 10 ms. A flag channel check (chchk), an error checking signal, goes high when a timeout error is detected and stays high until next bus address latch enable (bale) signal. The channel check flag is used to drive a transistor 230, which pulls the chchk_n (channel check negative) line low on the ISA bus. This inversion is needed to match signals internal to the STC circuit to signal conventions outside the STC circuit.

```
always @(posedge timeout_trig or negedge reset_n or posedge bale)
begin
    if(reset_n == 1'b0 || bale == 1'b1)
        chchk <= 1'b0;
    else begin
        chchk <= 1'b1;
    end
end
```

The ISA Control Interface for the STC is a 16-bit ISA bus interface with a base address of 300 H. The STC will only respond to IO Write and IO Read commands to correct addresses on the interface. The circuit may operate with either 16-bit input-output data (preferred) or 8-bit data. When 16-bit operation is selected the io 16_n flag is driven low to indicate that a 16-bit interface card is being used. Otherwise io 16_n remains high. Floating point convention is handled by the external tri-state (level shifters) driven from grab_bus_n.

assign *io16_n*=chip_select_gated?1*'b*0:1*'b* 1;

When the STC has been selected for a data transfer or command from the host computer, flag channel ready (chrdy) is driven high to have the shortest number of wait states. If a flag busy is high, channel ready remains low to accommodate more wait states. Read commands are not delayed by the state of the busy flag.

assign chrdy=~busy;

Register Block Interface is part of the STC control interface 300 that provides bi-directional data bus buffers. For a data read, if chip_select_gated is set, and iorc_n is not set, a "read with chip select" bit is set. Upon determining that reset or chip select is low or false, read_select is set to low or false. Then, if read_select is true, the circuit transfers data from input register read data (reg_rdata) to data_internal, the internal data bus, and in turn routed to the ISA bus. If read_select is not true, data internal is filled with a placeholder constant which disconnects the control interface 300 from the ISA bus. SD is assigned the value of data_internal.

```
always @(chip_select_gated or iorc_n) begin
    if(chip_select_gated == 1'b1 && iorc_n == 1'b0)
        read_with_cs = 1'b1;
    else
        read_with_cs = 1'b0;
end
always @(posedge read_with_cs or negedge reset_n or
negedge chip_select) begin
    if(reset_n == 1'b0 || chip_select == 1'b0)
        read_select <= 1'b0;
    else
        read_select <= 1'b1;
end
always @(read_select or reg_rdata) begin
    if(read_select == 1'b1)
        data_internal = reg_rdata;
    else
        data_internal = 16'bzzzzzzzzzzzzzzzz;
end
assign sd = data_internal;
assign reg_wdata = (reg_r_w_n == 1'b0) ?
sd : 16'bzzzz_zzzz_zzzz_zzzz;
assign read_select_n = ~read_select;
```

A similar pattern is followed for write commands. When iowc_n (write) goes low then register read/write signal is set to write, otherwise the default condition is to read. The circuit returns to read on chip_select inactive.

```
always @(chip_select_gated or iowc_n) begin
    if(chip_select_gated == 1'b1 && iowc_n == 1'b0)
        write_with_cs = 1'b1;
    else
        write_with_cs = 1'b0;
end
always @(posedge write_with_cs or negedge reset_n or
negedge chip_select) begin
    if(reset_n == 1'b0 || chip_select == 1'b0)
        reg_r_w_n <= 1'b1;
    else
        reg_r_w_n <= 1'b0;
end
```

A rising edge of the signal command_active is when the write occurs. In this context, register write strobe does not refer to the strobe lights, but to the immediate execution of the write command.

```
always @(cs_gated_went_low or chrdy or reg_r_w_n) begin
    if(chrdy == 1'b1 && reg_r_w_n == 1'b0)
        reg_wstrobe = cs_gated_went_low;
    else
        reg_wstrobe = 1'b0;
end
```

Control Register

The control register 302 receives and stores parameters for sessions as sent from the host computer through the control interface 300. These parameters comprise the timing or delay of the beginning of a phenomenon from a fixed point on the rotor or filler, and the duration of phenomenon. A phenomenon may be a lighting pulse, either top or bottom and involving one or more LEDs or sets of LEDs, or may be the shutter activation of the camera. Sets of LEDs may be distinguished by color, thus allowing the color of a lighting pulse to be adjusted as well. For clarity, representative examples of logic for the control registers will be given.

Register Write Control stores information for various parameters, such as PULSE_CFG (R/W), which is a pulse configuration. Upon detection of the positive edge of the write strobe signal or a negative edge of a reset signal, the PULSE_CFG (pulse configuration) data is cleared or reset in response to a reset signal, or receives data in response to the write signal.

```
always @(posedge wstrobe or negedge reset_n) begin
    if(reset_n == 1'b0)
        PULSE_CFG <= PULSE_CFG_reset;
    else
        if(addr == PULSE_CFG_addr && r_w_n == 1'b0)
            PULSE_CFG <= wdata[11:0];
end
```

SW_RESET or software reset is responsive to signals from the host computer to cause low pulse on sw_reset_n to resets all parameters to default values and resets the circuits to the power-up state.

```
always @(posedge wstrobe or negedge hw_reset_n or negedge
reset_n or posedge sw_reset_done) begin
    if(hw_reset_n == 1'b0 || reset_n == 1'b0 || sw_reset_done == 1'b1)
        sw_reset_n <= 1'b1;
    else begin
        if(wstrobe == 1'b1 && addr == SW_RESET_addr &&
        r_w_n == 1'b0 &&
            wdata[7:0] == 8'h55 && wdata[15:8] == 8'hAA)
            sw_reset_n <= 1'b0;
        else
            sw_reset_n <= 1'b1;
    end
end
always @(posedge clk or negedge reset_n) begin
    if(reset_n == 1'b0)
        sw_reset_running <= 1'b0;
    else
        if(sw_reset_n == 1'b0)
            sw_reset_running <= 1'b1;
        else
            sw_reset_running <= 1'b0;
end
always @(negedge clk or negedge reset_n) begin
    if(reset_n == 1'b0)
        sw_reset_done <= 1'b0;
    else
        if(sw_reset_running == 1'b1)
            sw_reset_done <= 1'b1;
        else
            sw_reset_done <= 1'b0;
end
```

STAT (R/W1) register holds information on the status of the lights and camera. Each bit is changed or latched individually and are only reset when the host computer writes a logic high (1) to a specified bit. This gives a positive indication that the host computer has acquired the information. A similar process is used for each of eight bits, 7 through 0. For clarity, the logic for representative bit 7 is shown.

```
assign stat7 = status[7:7];
always @(posedge wstrobe or posedge stat7 or negedge reset_n) begin
    if(reset_n == 1'b0)
        STAT[7:7] <= STAT_reset[7:7];
    else
        if(stat7 == 1'b1)
            STAT[7:7] <= 1'b1;
        else
            if(addr == STAT_addr && r_w_n == 1'b0)
                if(wdata[7:7] == 1'b1)
                    STAT[7:7] <= 1'b0;
end
```

A session for the lighting comprises a trigger (TRIG), an outputs enable, color select and sessions status (OE_STAT), an automatic ½× mode switch over (SW), a set of delays (DEL) for top and bottom lights and for the camera, and a similar set of pulse widths (PW) for the strobe lights and the camera shutter. Since these parameters are logically similar, only the logic for one session and only for the top lights during that session will be described in detail. One of skill in the art will be able to extend the example to the bottom lights and the camera and to multiple sessions, as contemplated in FIG. 5. The session 1 trigger, SES1_TRIG (R/W), establishes a rotational delay from a fixed point on the filler (rotor) before the start of a session.

```
always @(posedge wstrobe or negedge reset_n) begin
    if(reset_n == 1'b0)
        SES1_TRIG <= SES1_TRIG_reset;
    else
        if(addr == SES1_TRIG_addr & r_w_n == 1'b0)
            SES1_TRIG <= wdata[15:0];
end
```

The session output enable, color select and session status register, SES1_OE_STAT, comprises bits which specify the devices used in the session (camera, top or bottom strobe lights, or user strobe lights), the color to be used, and the status such as ½× mode, override of trigger due to conditions such as filler rotation direction, filler RPM, or mismatch of operating parameters.

```
assign SES1_OE = SES1_OE_STAT[11:0];
always @(posedge wstrobe or negedge reset_n) begin
    if(reset_n == 1'b0)
        SES1_OE_STAT[11:0] <= SES1_OE_STAT_reset[11:0];
    else
        if(addr == SES1_OE_STAT_addr && r_w_n == 1'b0)
            SES1_OE_STAT[11:0] <= wdata[11:0];
end
```

The automatic ½× mode switch over, SES1_SW, controls change between 1× and ½× modes. By default, the STC 190 assumes the user wants all Session triggers to occur on every rotation of the filler, called 1× mode. Because of high rotation speeds and other hardware limitations, the STC may trigger sessions on every other rotation, called ½× mode. Moreover, multiple sessions may be designated for either even or odd rotations of the filler, thus giving more temporal separation between sessions.

```
always @(posedge wstrobe or negedge reset_n) begin
    if(reset_n == 1'b0)
        SES1_SW <= SES1_SW_reset;
    else
        if(addr == SES1_SW_addr && r_w_n == 1'b0)
            SES1_SW <= wdata[15:0];
end
```

The session delay (DEL) may be used to establish a rotational delay from the session trigger for any of the hardware components such as the top lights, the bottom lights, the user lights or the camera. As an example, the session 1 top lights delay, SES1_T_DEL (R/W), is given here.

```
always @(posedge wstrobe or negedge reset_n) begin
    if(reset_n == 1'b0)
        SES1_T_DEL <= SES1_T_DEL_reset;
    else
        if(addr == SES1_T_DEL_addr && r_w_n == 1'b0)
            SES1_T_DEL <= wdata[14:0];
end
```

Similarly, the session pulse width (PW) may be used to establish a duration of operation, or pulse width, from the delay for any of the hardware components such as the top lights, the bottom lights, the user lights or the camera. As an example, the session 1 top lights pulse width, SES1_T_PW (R/W), is given here.

```
always @(posedge wstrobe or negedge reset_n) begin
    if(reset_n == 1'b0)
        SES1_T_PW <= SES1_T_PW_reset;
    else
        if(addr == SES1_T_PW_addr && r_w_n == 1'b0)
            SES1_T_PW <= wdata[9:0];
end
```

Filler position, FILLER_POS (read only, reset not applicable) is a data register recording the current location of the filler. Activation of hardware components such as the lights and the camera depend on the filler position and the control circuit can use this data to make decisions on when to change other parameters.

```
always @(posedge clk or negedge reset_n) begin
    if(reset_n == 1'b0)
        FILLER_POS_held <= 0;
    else
        FILLER_POS_held <= filler_pos;
end
```

A further data register maintained in the control registers 302 is the filler rotation time, FILLER_ROT_TIME. This data is latched once per rotation. Below a selected speed, for example 40 RPM, the rotation time will be zero.

```
always @(poedge clk or negedge reset_n) begin
    if(reset_n == 1'b0)
```
-continued
```
        FILLER_ROT_TIME_held <= 0;
    else
        FILLER_ROT_TIME_held <= filler_rot_time;
end
```

An encoder handler 304, which interprets the physical position of the filler from the centrifuge motor encoder 188, and an encoder emulator 306, which provides test signals that mimic the motor encoder without requiring rotation of the centrifuge, will be discussed more fully below. The control register 302 maintains a data register, ENC_EMU, for selecting between the output of the encoder handler 304 and the encoder emulator 306 and for setting parameters for the encoder emulator.

```
always @(posedge clk or negedge reset_n)begin
    if(reset_n == 1'b0)
        ENC_EMU <= ENC_EMU_reset
    else
        if(addr == ENC_EMU_addr&&r_w_n == 1'b0)
            ENC_EMU <= wdata[15:0]
```

Encoder Handler

In addition to the information contained in the control registers 302, preparation of session commands depends on the position of the filler. The position, speed and direction of the filler are determined by an encoder handler 304, in conjunction with sensor signals from the centrifuge motor encoder 188. The motor encoder produces three signals, called quadrature signals: an "a" signal and a "b" signal, which are temporally off-set square waves keyed to 2048 positions for one revolution of the centrifuge motor. The filler turns at twice the speed of the motor. The state and sequence of the a and b signals indicates speed and direction of rotation. For example, the sequence a off, b off; then a on, b off; then a on, b on; then a off, b on might indicate rotation in a clockwise direction. The sequence a off, b off, then a off, b on, then a on, b on, then a on, b off might indicate rotation in a counter-clockwise direction. The third signal is a "z" signal, which is produced once for every revolution of the motor. The "a" and "b" signals can be counted from the z signal to determine the position of the filler.

For test purposes, the input on the abz lines may be ignored, allowing the use of an encoder emulator 306, which produces abz signals for test purposes without turning the filler or motor. The encoder emulator will be described hereafter.

```
assign a_int = a & ~ignore_encoder;
assign b_int = b & ~ignore_encoder;
assign z_int = z & ~ignore_encoder;
```

The encoder 304 comprises digital filters to reject noise on quadrature signals. The signal must be stable for 3 clock cycles to be seen as a valid level. Channel a is illustrated below. Similar filters may be applied to the b and z signals.

```
always @(negedge clk or negedge reset_n) begin
    if(reset_n == 1'b0) begin
```

```
            a_history <= 3'b0;
        end else begin
            a_history <= a_history <<1;
            a_history[0:0] <= a_int;
        end
    end
    always @(posedge clk or negedge reset_n) begin
        if(reset_n == 1'b0)
            a_filt <= 1'b0;
        else begin
            case (a_history[2:0])
                3'b000:a_filt <= 1'b0;
                3'b111:a_filt <= 1'b1;
            endcase
        end
```

A motion state machine determines the direction of rotation, as described above and as illustrated in the following table, from the state of the a and b signals.

| STATE | FWD AB | RE AB |
|---|---|---|
| 0 | 00 | 00 |
| 1 | 10 | 01 |
| 2 | 11 | 11 |
| 3 | 01 | 10 |

The encoder handler 304 decodes conditions and outputs to recognize the progression of the filler from state to state. All inputs change on positive clock signal edge.

```
    always @(current_state or a_flit or b_flit) begin
        next_state = current_state;
        case(current_state)
            S0: begin
                if(a_flit == 1'b1) begin
                    next_state = S1;
                end else begin
                    if(b_flit == 1'b1) begin
                        next_state = S3;
                    end
                end
            end
            S1: begin
                if(b_flit == 1'b1) begin
                    next_state = S2;
                end else begin
                    if(a_flit == 1'b0) begin
                        next_state = S0;
                    end
                end
            end
            S2: begin
                if(a_flit == 1'b0) begin
                    next_state_S3;
                end else begin
                    if(b_flit == 1'b0) begin
                        next_state = S1;
                    end
                end
            end
            S3: begin
                if(b_flit == 1'b0) begin
                    next_state = S0;
                end else begin
                    if(a_flit == 1'b1) begin
                        next_state = S2;
                    end
                end
            end
        endcase
    end
```

A current state latch records the changing state, unless a reset signal causes both the current_state and current_state_history to be cleared.

```
    always @(negedge clk or negedge reset_n) begin
        if(reset_n == 1'b0) begin
            current_state_history <= S0;
            current_state <= S0;
        end else begin
            current_state_history <= current_state;
            current_state <= next_state;
        end
    end
```

A filler direction latch can be set by examining the ordered pair comprising the current_state_history (i.e., the last state) and the current_state. The direction of rotation is determined to be either clockwise or counter-clockwise, notated by one or zero in the data bit filler_direction.

```
    always @(posedge clk or negedge reset_n) begin
        if(reset_n == 1'b0)
            filler_direction <= 1'b0;
        else begin
            if(current_state_history != current_state) begin
                case( {current_state_history,current_state})
                    {S0,S1}: filler_direction <= 1'b1;
                    {S0,S3}: filler_direction <= 1'b0;
                    {S1,S2}: filler_direction <= 1'b1;
                    {S1,S0}: filler_direction <= 1'b0;
                    {S2,S3}: filler_direction <= 1'b1;
                    {S2,S1}: filler_direction <= 1'b0;
                    {S3,S0}: filler_direction <= 1'b1;
                    {S3,S2}: filler_direction <= 1'b0;
                endcase
            end
    end
```

A state changed is set to one (1) when filler motion is detected, or set to zero (0) when there is either no motion or a reset signal is received.

```
    always @(posedge clk or negedge reset_n) begin
        if(reset_n == 1'b0) begin
            state_changed <= 0;
        end else begin
            if(current_state_history != current_state)
                state_changed <= 1'b1;
            else
                state_changed <= 1'b0;
        end
```

A count clock is set to pulse after every change of state.

```
    always @(negedge clk or negedge reset_n) begin
        if(reset_n == 1'b0)
```

```
            count_clk <= 0;
        else begin
            if(state_changed == 1'b1)
                count_clk <= 1'b1;
            else
                count_clk <= 1'b0;
        end
```

A counter maintains the position of the filler. Since the motor only turns once for every two full turns of the filler, this counter rolls over between z signals and resets on every z signal for absolute reference.

```
assign filler_pos_clr = z_timer_clr;
always @(posedge count_clk or negedge reset_n
    or posedge filler_pos_clr) begin
    if(reset_n == 1'b0 || filler_pos_clr == 1'b1)
        filler_pos <= 0;
    else
        if(filler_direction == 1'b1)
            filler_pos <= filler_pos + 1;
        else
            filler_pos <= filler_pos - 1;
```

Because sessions may be triggered only on every second cycle and because it may be desirable to trigger different sessions on different cycles, the encoder handler 304 creates a filler_cycle to keep track of even/odd rotation of the filler for use in ½× mode.

```
always @(posedge clk or negedge reset_n) begin
    if(reset_n == 1'b0)
        filler_at_0 <= 1'b0;
    else begin
        if(filler_pos == 0)
            filler_at_0 <= 1'b1;
        else
            filler_at_0 <= 1'b0;
    end
end
always @(posedge filler_at_0 or negedge reset_n) begin
    if(reset_n == 1'b0)
        filler_cycle <= 0;
    else
        filler_cycle <= ~filler_cycle;
end
```

A timer, z_timer, counts 51.2 μs intervals between z signals to obtain the speed of rotation.

```
always @(posedge clk_51_2us or negedge
    reset_n or posedge z_timer_clr) begin
    if(reset_n == 1'b0 || z_timer_clr == 1'b1) begin
        z_timer <= 0;
        z_timeout <= 0;
    end else begin
        if(z_timer_hold != Z_TIMEOUT_MAX) begin
            z_timer <= z_timer + 1;
            z_timeout <= 0;
        end else
            z_timeout <= 1'b1;
    end
end
always @(negedge clk_51_2us or negedge reset_n) begin
```

```
    if(reset_n == 1'b0)
        z_timer_hold <= 0;
    else
        z_timer_hold <= z_timer;
end
```

The encoder handler 304 sets z_timer_latch high starting with the first falling clock edge after detection of the z signal. The latch is reset low when the z signal goes low.

```
assign z_timer_reset = (reset_n & z_filt);
always @(negedge clk or negedge z_timer_reset) begin
    if(z_timer_reset == 1'b0)
        z_timer_latch <= 0;
    else
        if(z_filt == 1'b1)
            z_timer_latch <= 1'b1;
end
```

The rotation time of the filler is calculated as one half the time since the z signal (due to the two-to-one ratio of motor speed to filler speed), if the filler is rotating in a selected direction. If the filler is rotating in the opposite direction, the rotation time is set to zero

```
always @(posedge z_timer_latch or posedge z_timeout
    or negedge reset_n) begin
    if(reset_n == 1'b0)
        filler_rot_time <= 0;
    else
        if((filler_direction != 1'b1) || (z_timeout == 1'b1))
            filler_rot_time <= 0;
        else
            filler_rot_time <= z_timer / 2;
end
```

When a new z signal is received, z_timer_clr is set at the first rising clock edge after z_timer_latch high. The clear z timer signal is disabled on the next falling clock edge. The encoder handler responds to this signal by resetting the z timer.

```
always @(posedge clk or negedge reset_n or
    negedge z_timer_latch or posedge reset_z_timer_clr) begin
    if(reset_n == 1'b0 || z_timer_latch == 1'b0 ||
        reset_z_timer_clr == 1'b1)
        z_timer_clr <= 0;
    else
        z_timer_clr <= 1'b1;
end
always @(negedge clk or negedge reset_n or negedge z_timer_latch)
begin
    if(reset_n == 1'b0 || z_timer_latch == 1'b0)
        reset_z_timer_clr <= 0;
    else
        reset_z_timer_clr <= 1'b1;
end
endmodule
```

Encoder Emulator

The STC may have a circuit for emulating the functionality of a motor encoder. The emulator circuit may allow for bench testing and possible self-testing or calibration without needing to actually spin the filler motor. The emulator circuit may produce 3 TTL signals (A_tst, B_tst, Z_tst) that emulate the signals from a standard motor encoder. The A_tst and B_tst signals emulate the quadrature signals from a 2048 position encoder. The Z_tst signal emulates a single pulse per revolution absolute positional reference. Jumpers or computer-controlled switches may allow these signals to be routed to the motor encoder inputs. The emulator may also produce signals typical of a selected direction of rotation. The control computer may turn the emulator on or off. The control computer may select from several speeds (filler RPM) for the emulator circuit to emulate. These speeds may range from 0 RPM to 3000 RPM but do not have to allow for every possible value.

The encoder emulator 306 comprises a logical gate that passes either the actual a, b, and z signals or information derived therefrom as processed by the encoder handler 304 or test signals A_tst, B_tst, and Z_tst to the session control circuits 308, 310, 312, and 314.

```
assign loopback = ENC_EMU[9:9];
always @(A or A_tst or loopback) begin
    if(loopback == 1'b0)
        A_enc = A;
    else
        A_enc = A_tst;
end
always @(B or B_tst or loopback) begin
    if(loopback == 1'b0)
        B_enc = B;
    else
        B_enc = B_tst;
end
always @(Z or Z_tst or loopback) begin
    if(loopback == 1'b0)
        Z_enc = Z;
    else
        Z_enc = Z_tst;
end
```

The encoder emulator sets an artificial encoder clock value or count to be used instead of an actual z signal timer as described above in connection with the encoder handler 304. Using circuit logic similar to the encoder handler, a test signal is produced that allows the apparatus to be tested without rotating the filler.

Session Control

A plurality of session control circuits, such as session 1 control 308, session 2 control 310, session 3 control 312, or session 4 control 314, receive input from the encoder handler 304 or encoder emulator 306 to establish a session trigger, that is, the point on the filler rotation when a session should occur, and input from the control registers 302 to establish the session events, that is, the combination of strobe lights and camera events that should occur during a session. A session trigger is a selected position on the filler to start session timers to pulse the strobe lights and to activate the camera. From a zero position on the motor encoder 188, rotation of the filler is divided into segments, for example 4096 segments, from which the position of the filler may be determined. In addition, the trigger depends on whether 1× mode or ½× mode has been selected, either manually or automatically at predetermined speeds.

The session control 308, 310, 312, 314, accommodates switchover from 1× to ½× modes at selected RPM, as well as accommodating manual switchover to ½× mode.

```
always @(posedge clk_10MHz or negedge reset_n) begin
    if(reset_n == 1'b0)
        switch_to_halfX <= 1'b0;
    else begin
        if(filler_rot_time < SES_SW[10:0] && filler_rot_time != 15'b0)
            switch_to_halfX <= 1'b1;
        else
            switch_to_halfX <= 1'b0;
    end
end
always @(posedge clk_10MHz or negedge reset_n) begin
    if(reset_n == 1'b0)
        switch_to_1X <= 1'b0;
    else begin
        if((filler_rot_time > (SES_SW[10:0]+(SES_SW[15:11]<<2))) &&
            (filler_rot_time != 15'b0))
            switch_to_1X <= 1'b1;
        else
            switch_to_1X <= 1'b0;
    end
end
always @(posedge clk_10MHz or negedge reset_n) begin
    if(reset_n == 1'b0)
        auto_off <= 1'b0;
    else begin
        if(SES_SW[10:0] == 11'h000)
            auto_off <= 1'b1;
        else
            auto_off <= 1'b0;
    end
end
assign man_halfX = SES_TRIG[12:12];
always @(posedge clk_10MHz or negedge reset_n) begin
    if(reset_n == 1'b0)
        session_mode <= 1'b0;
    else begin
        if(man_halfX == 1'b1)
            session_mode <= 1'b0; // 1/2X mode manual
        else begin
            // auto switchover is off if setting in register is 0
            if(auto_off == 1'b1)
                session_mode <= 1'b1; // 1X mode
            else begin
                if(switch_to_halfX) begin
                    session_mode <= 1'b0; // 1/2X mode auto
                end else begin
                    if(switch_to_1X)
                        session_mode <= 1'b1; // 1x mode swichback
                end
```

A session trigger must be disabled upon the occurrence of certain operating conditions. For example, a session cannot trigger if a reset signal is received, or if the RPM of the filler is less than 100 (a count of 11718 equals 100.006 RPM) SES_TRIG[15], or if the filler direction of rotation is incorrect (specified by SES_TRIG[14]), or if ½× mode and filler_cycle do not match (SES_TRIG[13]); or if none of the pulse width setting are greater than zero; or when the data bit wait_for_filler_move is high, which prevents retriggering when the filler is in the same position.

```
always @(posedge clk_10MHz or negedge reset_n) begin
    if(reset_n == 1'b0)
        no_session_trig <= 1'b1;
    else begin
        if((filler_rot_time > 15'd11718) || (filler_rot_time == 15'd0) ||
            (SES_TRIG[15:15] == 1'b1) ||
            (filler_direction != SES_TRIG[14:14]) ||
            (session_mode == 1'b0 && filler_cycle !=
            SES_TRIG[13:13]) ||
            (SES_C_PW == 15'b0 && SES_T_PW == 10'b0 &&
```

```
    SES_B_PW == 10'b0 && SES_U_PW == 16'b0) ||
         (wait_for_filler_move == 1'b1)
         )
         no_session_trig <= 1'b1;
    else
         no_session_trig <= 1'b0;
    end
```

In the illustrated embodiment, a session trigger pulses high when filler_pos matches the data register SES_TRIG. Timing for other parameters of a session starts when trigger goes low.

```
always @(negedge clk_10MHz or negedge reset_n) begin
    if(reset_n == 1'b0)
         session_trigger <= 1'b0;
    else
         if(filler_pos == SES_TRIG[11:0] && no_session_trig != 1'b1 &&
            session_running == 1'b0)
              session_trigger <= 1'b1;
         else
              session_trigger <= 1'b0;
end
```

A data bit session running is high throughout a session (until all channels complete).

```
always @(posedge session_trigger or posedge session_done or
         negedge reset_n) begin
    if(reset_n == 1'b0 || session_done == 1'b1)
         session_running <= 1'b0;
    else
         session_running <= 1'b1;
    end
assign busy = session_running;
```

A data bit session_done pulses high at the end, or count down to zero, of all timers.

```
always @(negedge clk_10MHz or negedge reset_n) begin
    if(reset_n == 1'b0)
         session_done <= 1'b0;
    else
         if(session_running == 1'b1 && session_trigger != 1'b1 &&
            ce_delay_timer == 0 && ce_pw_timer == 0 &&
            ts_delay_timer == 0 && ts_pw_timer == 0 &&
            bs_delay_timer == 0 && bs_pw_timer == 0 )
              session_done <= 1'b1;
         else
              session_done <= 1'b0;
    end
```

A data bit wait_for_filler_move is created to disable retrigger of a session when the filler has not moved, but a session is done. This prevents an error if the filler rotation is too slow or stops for any reason.

```
always @(posedge session_trigger or negedge reset_n) begin
    if(reset_n == 1'b0)
         last_trig_filler_pos <= 12'b0;
    else
         last_trig_filler_pos <= filler_pos;
    end
always @(posedge clk_10MHz or negedge reset_n) begin
    if(reset_n == 1'b0)
         wait_for_filler_move <= 1'b1;
    else begin
         if(filler_pos == last_trig_filler_pos)
              wait_for_filler_move <= 1'b1;
         else
              wait_for_filler_move <= 1'b0;
    end
```

Strobe Light Timing

After a session trigger, output timing needs to properly activate and operate the top or bottom strobe lights. The STC provides a software-selectable delay from whenever a session trigger occurs to when a strobe light pulse signal is activated. This delay may range from at least 0 μs to 3 ms with 0.1 μs resolution. The STC supports a software-selectable delay from whenever a top strobe light trigger pulse is activated until it is de-activated, thereby establishing a pulse width. This pulse width ranges from 0 μs to at least 100 μs with 0.1 μs resolution. The STC also supports a software-selectable configuration setting for the polarity of the top strobe light trigger pulse (default positive pulse). In the presently preferred embodiment, the STC may activate any combination of four top strobe outputs (e.g., top_strobe_1, top_strobe_2, top_strobe_3, and top_strobe_4). This means that the four possible outputs do not have independent timing. Additional or fewer combinations may be provided without departing from the teachings hereof. Similar combinations may be provided for the bottom strobe lights. In addition a user strobe light may be provided to allow a user to view the filler under stroboscopic lighting.

Delay timers setting a time from Session Trigger to start of pulse on each channel, that is, for the camera, top strobe lights and bottom strobe lights, are all based on a 10 MHz clock (0.1 μs steps). An example is given herein for the camera, ce_delay_timer. Similar logic would be used for the top strobe lights (ts_delay_timer) or for the bottom strobe lights (bs_delay_timer).

```
always @(posedge clk_10MHz or negedge reset_n) begin
    if(reset_n == 1'b0)
         ce_delay_timer <= 0;
    else
         if(session_trigger == 1'b1 && SES_C_PW >0)
              ce_delay_timer <= SES_C_DEL+1;
         else
              if(ce_delay_timer > 0)
                   ce_delay_timer <= ce_delay_timer - 1;
    end
```

Start signals are given for output stage to activate hardware elements. Top and bottom strobe start signals are generated in the same way as the camera start signal shown here. The start signal ce_start will not go high if the related pulse width setting is zero.

```
always @(negedge clk_10MHz or negedge reset_n) begin
    if(reset_n == 1'b0)
         ce_start <= 0;
```

-continued

```
        else begin
            if(ce_delay_timer == 15'h0001)
                ce_start <= 1'b1;
            else
                ce_start <= 1'b0;
        end
    end
```

Pulse width timers set time durations from the start of a pulse to the end of the pulse on each channel. All are based on 10 MHz clock (0.1 us steps)—count starts 1 clock signal after load, which is 1 clock signal after the session trigger.

```
always @(posedge clk_10MHz or negedge reset_n) begin
    if(reset_n == 1'b0)
        ce_pw_timer <= 0;
    else begin
        if(session_trigger == 1'b1 && SES_C_PW >0)
            ce_pw_timer <= (SES_C_PW*10) + 1; // result is +0, −1
                on resolution
        else
            if((ce_pw_timer > 0 && camera_enable_int == 1'b1) ||
                (ce_pw_timer == 20'd1 && camera_enable_int == 1'b0))
                ce_pw_timer <= ce_pw_timer − 1;
    end
end
```

After the pulse width timer counts down, an end signal is produced for the output stage of session control.

```
always @(negedge clk_10MHz or negedge reset_n) begin
    if(reset_n == 1'b0)
        ce_end <= 0;
    else begin
        if(ce_pw_timer == 15'h0001 && camera_enable_int == 1'b1)
            ce_end <= 1'b1;
        else
            ce_end <= 1'b0;
    end
end
```

Before signals are sent to an output stage 316 for execution, the session control makes a final check for an interrupt signal or for a signal indicating the end of use of the hardware, in the illustrated case, end of use of the camera, by creating a square wave control pulse. The pulse commences with the occurrence of the ce_start signal and ends with a ce_end signal. A reset signal can, of course, interrupt the process.

```
always @(posedge ce_start or posedge ce_end or negedge reset_n )
begin
    if(reset_n == 1'b0 || ce_end == 1'b1)
        camera_enable_int <= 1'b0;
    else
        camera_enable_int <= 1'b1;
end
```

Finally, a session control circuit 308, 310, 312, 314, enables the outputs through session output enable, SES_OE, for top or bottom lights, including colors, and for enable camera in response to settings in registers. In this instance all channels of the presently preferred embodiment are shown.

```
assign bottom_strobe_2 = SES_OE[9] & SES_OE[3:3] &
    bottom_strobe_int;
assign bottom_strobe_1 = SES_OE[8] & SES_OE[3:3] &
    bottom_strobe_int;
assign top_strobe_4 = SES_OE[7] & SES_OE[2:2] & top_strobe_int;
assign top_strobe_3 = SES_OE[6] & SES_OE[2:2] & top_strobe_int;
assign top_strobe_2 = SES_OE[5] & SES_OE[2:2] & top_strobe_int;
assign top_strobe_1 = SES_OE[4] & SES_OE[2:2] & top_strobe_int;
assign camera_enable = camera_enable_int & SES_OE[1:1];
```

Bottom Strobe Light Timing

Similarly, after a session trigger, output timing needs to properly activate and operate the bottom strobe light. The STC provides a software-selectable delay from whenever a session trigger occurs to when the bottom strobe light trigger pulse signal is activated. This delay may range from at least 0 µs to 3 ms with 0.1 µs resolution. The STC supports a software-selectable delay from whenever a bottom strobe light trigger pulse is activated until it is de-activated, that is until the end of the pulse width. This pulse width ranges from 0µs to at least 100 µs with 0.1 µs resolution. The STC provides a software-selectable configuration setting for the polarity of the bottom strobe light trigger pulse (default positive pulse). The STC may activate any combination of four outputs (e.g., bottom_strobe_1, bottom_strobe_2, bottom_strobe_3, and bottom_strobe_4). This means that the four possible outputs cannot have independent timing.

User Strobe Light Timing

A user strobe light 37, illuminating the filler so that an operator or user can observe the fluid in the apparatus, may also be provided, as shown in FIGS. 5 and 7. Where a user strobe is used, output timing will be needed after a session trigger to properly activate and operate the user strobe light. The STC may provide a software-selectable delay from whenever a session trigger occurs to when the user strobe light trigger pulse signal is activated. This delay may ranges from at least 0 µs to 3 ms with 0.1 µs resolution. The STC provides a software selectable delay from whenever a user strobe light trigger pulse is activated until it is de-activated, that is, until the end of the pulse width. This pulse width may range from at least 0 ms to 60 ms with 1.0 µs resolution. The STC also provides a software-selectable configuration setting for the polarity of the User Strobe Light Trigger Pulse (default positive pulse).

The user strobe light 37 allows operator control of the interface between fluid phases, as is known in the art. Should the automatic controls described herein be interrupted for any reason, an operator could continue processing using the user strobe light. For control of the specific user strobe light preferred herein, a separate synchronization and timing controller 192' may be provided for redundancy. A less robust system, as known in the art, could also be provided. Both the main synchronization and timing controller 192 and the user strobe STC 192' may respond to signals 190 from the motor encoder 188 through an encoder handler. In addition, a Halls Effect magnetic sensor coupled to the filler or rotor may provide auxiliary signals 190', should the encoder fail for any reason. Signals 190' from the Halls Effect sensor may be processed 304' in a manner similar to the encoder handler 304. The session control 308 for the user strobe 37 could use either input, thus providing a further fail-safe condition.

Camera Enable and Timing

Camera enable and timing is an independent process initiated by a session trigger. The STC provides a single camera enable pulse output with a software-selectable delay from whenever a session trigger occurs to when the camera enable pulse is activated. This delay ranges from 0 μs to at least 3 ms with 0.1 μs resolution. The STC provides a software-selectable delay from whenever a camera enable pulse is activated until it is de-activated. This delay ranges from 0 ms to at least 30 ms with 1.0 μs resolution. The STC also provides a software configuration setting for the polarity of Camera Enable Pulse (default positive pulse).

Reset Handling

The STC may have two separate resets 318 available. A software reset may be triggered by writing a predefined code to the reset register. In addition, a hardware reset when driven low may perform a reset if the control interface is lost. The control computer may write to a Reset register to cause the STC to reset all counters and registers. The STC may provide for the hardware reset by driving a pin to logic low. This pin may be pulled high in normal operation with sufficient drive to ensure glitches on the reset input will not cause an unintentional reset to the STC. The hardware or the software reset returns to power up state requiring configuration of zero of the filler position and other initial procedures.

Output Control and Session Limits Handling

The optical monitoring system 10 is able to produce controlled stroboscopic lighting using LEDs that are driven beyond design limits of the LEDs for short periods of time. Because multiple sessions are permitted, sessions may overlap or occur too close together, overheating the LEDs or not allowing sufficient cooling between pulses. An output control 316 prevents such conditions by imposing limits on pulse durations, even if an extended duration is in response to multiple sessions, and by requiring certain time periods between pulses. The STC may have a hardware-selectable or software-selectable maximum pulse width limiter to de-activate the output pulse for any channel (top strobe light, bottom strobe light, user strobe light, and camera) if the time is exceeded. It is individually selectable for each of the two output channels. For the user strobe output, this limiter may be hardware or software selectable. For the camera enable output, the limiter may also be hardware or software selectable. The STC may also provide a minimum off time limiter to de-activate the output pulse for any channel if the off time would have been exceeded. This is particularly important in connection with the light sources using LEDs. In this apparatus, the LEDs are driven at higher than their rated power for short periods of time. To maintain operability, the LEDs must have sufficient time to recover after a period of activation. For the top and bottom strobe outputs, this limiter may be hardware or software selectable. It is individually selectable for each of the 2 output channels. For the user strobe output and for the camera enable output, this limiter may also be hardware or software. These limiters are meant for safety purposes, since with the ability to trigger multiple independent sessions in close succession, it is possible to overlap pulses for sessions, thereby extending pulse widths past the maximum settings for one session. If either error handler is activated for any channel, a status bit shall be set to notify the control computer of the condition. Error flags may be reset by software of the control computer or by hardware reset.

The output control circuit 316 combines the instructions from the session controls 308, 310, 312, and 314 and deactivates the outputs if necessary, as shown here for the camera.

```
always @(ses1_camera_enable or ses2_camera_enable
   or PULSE_CFG[0:0]) begin
      ce_comb_sig = PULSE_CFG[0:0] &
      (ses1_camera_enable | ses2_camera_enable);
   end
```

The strobe commands are also combined and limited, as shown here for the set 1 of the top strobe lights. Similar logic should be repeated for all other strobe sets.

```
always @(ses1_top_strobe_1 or ses2_top_strobe_1 or
   PULSE_CFG[1:1]) begin
      ts_comb_sig_1 = PULSE_CFG[1:1] &
      (ses1_top_strobe_1 | ses2_top_strobe_1);
   end
```

The combined signal (here, the camera combined signal) is stored as ce_comb_history for comparison hereafter.

```
always @(posedge clk_10MHz or negedge reset_n) begin
   if(reset_n == 1'b0)
      ce_comb_history <= 1'b0;
   else
      ce_comb_history <= ce_comb_sig;
   end
```

Pulse width limits are applied to limit the duration of use of the camera.

```
always @(posedge clk_10MHz or negedge reset_n) begin
   if(reset_n == 1'b0) begin
      ce_pwlim_count <= 1;
      ce_pwlim_count_on <= 1'b0;
   end else begin
      if(ce_comb_sig == 1'b1) begin
         if(ce_pwlim_count_on == 1'b0 && ce_comb_history == 1'b0)
         begin
            ce_pwlim_count <= PWLIM_CAMERA_SETTING;
            ce_pwlim_count_on <= 1'b1;
         end else begin // count down
            if(ce_pwlim_count != 0)
               ce_pwlim_count <= ce_pwlim_count-1;
         end
      end else begin
         ce_pwlim_count_on <= 1'b0;
      end
   end
end
always @(ce_pwlim_count or ce_pwlim_count_on) begin
   if(ce_pwlim_count == 0 && ce_pwlim_count_on == 1'b1)
      ce_pwlim = 1'b1;
   else
      ce_pwlim = 1'b0;
   end
```

Similarly, top strobe pulse width limits are applied. This circuit logic would be repeated for bottom strobe limits.

```
always @(posedge clk_10MHz or negedge reset_n) begin
   if(reset_n == 1'b0)
      ts_comb_history_1 <= 1'b0;
```

```
        else
            ts_comb_history_1 <= ts_comb_sig_1;
        end
always @(posedge clk_10MHz or negedge reset_n) begin
    if(reset_n == 1'b0) begin
        ts_pwlim_count_1 <= 1;
        ts_pwlim_count_on_1 <= 1'b0;
    end else begin
        if(ts_comb_sig_1 == 1'b1) begin
            if(ts_pwlim_count_on_1 == 1'b0 &&
              ts_comb_history_1 == 1'b0) begin
                ts_pwlim_count_1 <= PWLIM_TOP_SETTING;
                ts_pwlim_count_on_1 <= 1'b1;
            end else begin // count down
                if(ts_pwlim_count_1 != 0)
                    ts_pwlim_count_1 <= ts_pwlim_count_1-1;
            end
        end else begin
            ts_pwlim_count_on_1 <= 1'b0;
        end
    end
end
always @(ts_pwlim_count_1 or ts_pwlim_count_on_1) begin
    if(ts_pwlim_count_1 == 0 && ts_pwlim_count_on_1 == 1'b1)
        ts_pwlim_1 = 1'b1;
    else
        ts_pwlim_1 = 1'b0;
end
```

In addition to a maximum pulse width duration, a minimum time off or inactive period must also be enforced to permit the camera and strobe lights to cool or recover. The camera enable off time limiter uses ce_comb_history created above.

```
always @(posedge clk_10MHz or negedge reset_n) begin
    if(reset_n == 1'b0) begin
        ce_offlim_count <= 0;
        ce_offlim_count_on <= 1'b0;
    end else begin
        if(ce_comb_sig == 1'b0 || ce_offlim_count_on == 1'b1) begin
            if(ce_offlim_count_on == 1'b0 &&
              ce_comb_history == 1'b1) begin
                ce_offlim_count <= OFFLIM_CAMERA_SETTING;
                ce_offlim_count_on <= 1'b1;
            end else begin // count down
                if(ce_offlim_count != 0)
                    ce_offlim_count <= ce_offlim_count-1;
                else
                    ce_offlim_count_on <= 1'b0;
            end
        end
    end
end
always @(ce_offlim_count or ce_offlim_count_on) begin
    if(ce_offlim_count != 0 && ce_offlim_count_on == 1'b1)
        ce_offlim = 1'b1;
    else
        ce_offlim = 1'b0;
end
```

A top strobe off time limiter is exemplary of control for both top strobe lights and bottom strobe lights. The strobe off time limiter uses "ts_comb_history", created above.

```
always @(posedge clk_10MHz or negedge reset_n) begin
    if(reset_n == 1'b0) begin
        ts_offlim_count_1 <= 0;
        ts_offlim_count_on_1 <= 1'b0;
    end else begin
        if(ts_comb_sig_1 == 1'b0 || ts_offlim_count_on_1 ==
          1'b1) begin
            if(ts_offlim_count_on_1 == 1'b0 &&
              ts_comb_history_1 == 1'b1) begin
                ts_offlim_count_1 <= OFFLIM_TOP_SETTING;
                ts_offlim_count_on_1 <= 1'b1;
            end else begin // count down
                if(ts_offlim_count_1 != 0)
                    ts_offlim_count_1 <= ts_offlim_count_1-1;
                else
                    ts_offlim_count_on_1 <= 1'b0;
            end
        end
    end
end
always @(ts_offlim_count_1 or ts_offlim_count_on_1) begin
    if(ts_offlim_count_1 != 0 && ts_offlim_count_on_1 == 1'b1)
        ts_offlim_1 = 1'b1;
    else
        ts_offlim_1 = 1'b0;
end
```

The output control circuit 316 assembles the results for the tests for combined signals and minimum time off limits, forcing high output signals low if the limits are exceeded.

```
assign ce_offlim_trig = ce_comb_sig & ce_offlim;
assign ts_offlim_trig = ((ts_comb_sig_1 & ts_offlim_1) ||
    (ts_comb_sig_2 & ts_offlim_2) ||
    (ts_comb_sig_3 & ts_offlim_3) ||
    (ts_comb_sig_4 & ts_offlim_4));
assign bs_offlim_trig = ((bs_comb_sig_1 & bs_offlim_1) ||
    (bs_comb_sig_2 & bs_offlim_2));
```

The output control circuit 316 then collects signals to make a status bus.

```
assign ts_offlim = ts_offlim_1 | ts_offlim_2 | ts_offlim_3 |
    ts_offlim_4;
assign bs_offlim = bs_offlim_1 | bs_offlim_2;
assign ts_pwlim = ts_pwlim_1 | ts_pwlim_2 | ts_pwlim_3 |
    ts_pwlim_4;
assign bs_pwlim = bs_pwlim_1 | bs_pwlim_2;
assign status = {1'b0,
    bs_offlim_trig & ~disable_offlim,
    ts_offlim_trig & ~disable_offlim,
    ce_offlim_trig & ~disable_offlim,
    1'b0,
    bs_pwlim & ~disable_pwlim,
    ts_pwlim & ~disable_pwlim,
    ce_pwlim & ~disable_pwlim};
```

A second stage of the output control circuit deactivates pulses if either limiter triggers, as shown for the camera and a top strobe_1 set of LEDs.

```
always @(ce_comb_sig or
ce_pwlim or ce_offlim or disable_pwlim or disable_offlim)
begin
    ce_lim_sig = ce_comb_sig & ~(ce_pwlim & ~disable_pwlim) &
        ~(ce_offlim & ~disable_offlim);
end
```

The following top strobe_1 circuit logic may be repeated as often as necessary for other top strobe sets and for bottom strobe sets.

```
always @(ts_comb_sig_1 or ts_pwlim_1 or ts_offlim_1 or
disable_pwlim or disable_offlim) begin
    ts_lim_sig_1 = ts_comb_sig_1 &
        ~(ts_pwlim_1 & ~disable_pwlim) &
        ~(ts_offlim_1 & ~disable_offlim);
end
```

In a third stage, the output control circuit inverts the outputs, if necessary, for hardware compatibility between logic high and logic low segments of the apparatus as may be selected under software control.

```
always @(ce_lim_sig or PULSE_CFG[4:4] or disable_outputs_n)
begin
    if(PULSE_CFG[4:4] == 1'b1)
        camera_enable = ce_lim_sig & disable_outputs_n;
    else
        camera_enable = ~ce_lim_sig & disable_outputs_n;
end
```

The following top strobe_1 circuit logic may be repeated as often as necessary for other top strobe sets and for bottom strobe sets.

```
always @(ts_lim_sig_1 or PULSE_CFG[5:5] or disable_outputs_n)
begin
    if(PULSE_CFG[5:5] == 1'b1)
        top_strobe_1 = ts_lim_sig_1 & disable_outputs_n;
    else
        top_strobe_1 = ~ts_lim_sig_1 & disable_outputs_n;
end
```

The forgoing specification describes a centrifuge blood processing system for separating fluid components comprising a first light source comprising a plurality of light emitting diodes in optical communication with the centrifuge blood processing system for providing an incident light beam for illuminating an observation region on the centrifuge blood processing system, a light collection element in optical communication with said centrifuge blood processing system for collecting at least a portion of said light transmitted, scattered or both from said observation region, a programmable controller for providing an operational procedure for said monitoring system; and an independent dedicated control circuit in electrical communication with said programmable controller and electrically coupled to said light source, the control circuit receiving command parameters from the controller and controlling periods of illumination from the light source in response to the command parameters.

It will be apparent to those skilled in the art that various modifications and variations can be made to the structure and methodology of the present invention without departing from the scope or spirit of the invention. Thus, it should be understood that the invention is not limited by the examples discussed in the specification. Rather, the invention is intended to cover modifications and variations provided they come within the scope of the following claims and their equivalents.

We claim:

1. A monitoring system for a centrifuge blood processing system for separating fluid components and having a separation chamber rotating about a central rotation axis, comprising:
   a first light source in optical communication with said centrifuge blood processing system for providing an incident light beam for illuminating an observation region including at least part of said separation chamber, thereby generating light transmitted, scattered or both from said observation region;
   a light collection element in optical communication with said centrifuge blood processing system for collecting at least a portion of said light transmitted, scattered or both from said observation region;
   a programmable controller for providing an operational procedure for said monitoring system; and
   an independent dedicated control circuit in electrical communication with said programmable controller and electrically coupled to said first light source, said control circuit comprising means for receiving command parameters from said programmable controller and means for energizing said first light source at a first selected rotation and de-energizing said first light source after a selected duration.

2. The monitoring system of claim 1 further comprising an encoder coupled to said separation chamber, said encoder communicating a signal related to a rotational position of said separation chamber to said dedicated control circuit.

3. The monitoring system of claim 2 wherein said dedicated control circuit identifies an initial zero position of said separation chamber from said encoder signal.

4. The monitoring system of claim 3 wherein said dedicated control circuit initiates at least one illumination session commencing a selected rotation from said initial zero position.

5. The monitoring system of claim 3 wherein said initial zero position can be calibrated at any position along the rotation of the separation chamber.

6. The monitoring system of claim 2 further comprising a user stroboscopic light source, said user stroboscopic slight source being controlled by a user control circuit in response to signals from said encoder.

7. The monitoring system of claim 6 further comprising a Halls effect sensor coupled to said separation chamber, said Halls effect sensor communicating a signal related to a rotational position of said separation chamber to said dedicated control circuit.

8. The monitoring system of claim 1 wherein said first light source is an upper light source, and further comprising a lower light source and a monitoring camera, said camera having a shutter apparatus, and wherein said dedicated control circuit can control each of said upper light source, said lower light source and said monitoring camera.

9. The monitoring system of claim 1 further comprising a Halls effect sensor coupled to said separation chamber, said Halls effect sensor communicating a signal related to a rotational position of said separation chamber to said dedicated control circuit.

10. A monitoring system for a centrifuge blood processing system for separating fluid components and having a separation chamber rotating about a central rotation axis, comprising:
    a first light source in optical communication with said centrifuge blood processing system for providing an incident light beam for illuminating an observation region including at least part of said separation chamber, thereby generating light transmitted, scattered or both from said observation region;

a light collection element in optical communication with said centrifuge blood processing system for collecting at least a portion of said light transmitted, scattered or both from said observation region;

a programmable controller for providing an operational procedure for said monitoring system; and an independent dedicated control circuit in electrical communication with said programmable controller and electrically coupled to said first light source, said control circuit comprising means for receiving command parameters from said programmable controller and wherein said dedicated control circuit comprises means for providing a signal to said first light source to completely control the initiation, duration, intensity and termination of illumination from said first light source.

11. A monitoring system for a centrifuge blood processing system for separating fluid components and having a separation chamber rotating about a central rotation axis, comprising:

a first light source in optical communication with said centrifuge blood processing system for providing an incident light beam for illuminating an observation region including at least part of said separation chamber, thereby generating light transmitted, scattered or both from said observation region;

a light collection element in optical communication with said centrifuge blood processing system for collecting at least a portion of said light transmitted, scattered or both from said observation region;

a programmable controller for providing an operational procedure for said monitoring system; and an independent dedicated control circuit in electrical communication with said programmable controller and electrically coupled to said first light source, said control circuit comprising means for receiving command parameters from said programmable controller and comprising a first timer limiting the duration of a period of illumination from said first light source.

12. The monitoring system of claim 11 wherein said first light source comprises light-emitting diodes (LEDs) and wherein said duration of illumination is limited to prevent failure of said LEDs.

13. The monitoring system of claim 11 further comprising a second timer providing a minimum period between periods of illumination.

14. The monitoring system of claim 13 wherein said first light source comprises light-emitting diodes (LEDs) and wherein said duration of illumination and said minimum period between periods of illumination are selected to prevent failure of said LEDs.

15. A monitoring system for a centrifuge blood processing system for separating fluid components and having a separation chamber rotating about a central rotation axis, comprising:

a first light source in optical communication with said centrifuge blood processing system for providing an incident light beam for illuminating an observation region including at least part of said separation chamber, thereby generating light transmitted, scattered or both from said observation region;

a light collection element in optical communication with said centrifuge blood processing system for collecting at least a portion of said light transmitted, scattered or both from said observation region;

a programmable controller for providing an operational procedure for said monitoring system; and an independent dedicated control circuit in electrical communication with said programmable controller and electrically coupled to said first light source, said control circuit comprising means for receiving command parameters from said programmable controller and means for controlling a plurality of sessions comprising delays and periods of illumination.

16. The monitoring system of claim 15 wherein said dedicated control circuit comprises means for combining overlapping periods of illumination into a combined period of illumination.

17. The monitoring system of claim 16 further comprising a first timer limiting the duration of a period of illumination from said first light source.

18. The monitoring system of claim 17 wherein said first light source comprises light-emitting diodes (LEDs) and wherein said duration of illumination is limited to prevent failure of said LEDs.

19. The monitoring system of claim 18 further comprising a second timer providing a minimum period between periods of illumination.

20. The monitoring system of claim 19 wherein said first light source comprises light-emitting diodes (LEDs) and wherein said duration of illumination and said minimum period between periods of illumination are selected to prevent failure of said LEDs.

21. A centrifuge blood processing system for separating fluid components comprising a separation chamber a motor coupled to said separation chamber for rotating said chamber about a central rotation axis, a plurality of pumps for controlling fluid flow within said separation chamber, a controller in electrical communication with said pumps and said motor, said controller producing commands controlling said pumps and said motor, and a monitoring system in electrical communication with said controller and monitoring fluid in said separation chamber, said monitoring system comprising:

a first light source in optical communication with said blood processing system for providing an incident light beam for illuminating an observation region including at least part of said separation chamber, thereby generating light transmitted, scattered or both from said observation region;

a light collection element in optical communication with said centrifuge blood processing system for collecting at least a portion of said light transmitted, scattered or both from said observation region;

a programmable controller for providing an operational procedure for said monitoring system; and an independent dedicated control circuit in electrical communication with said programmable controller and electrically coupled to said first light source, said dedicated control circuit comprising means for receiving command parameters from said controller and means for completely controlling the initiation, duration, intensity and termination of illumination from said first light source.

22. The centrifuge blood processing system of claim 21 further comprising an encoder coupled to said separation chamber, said encoder communicating a signal related to a rotational position of said separation chamber to said dedicated control circuit.

23. The centrifuge blood processing system of claim 22 wherein said dedicated control circuit identifies an initial zero position of said separation chamber from said encoder signal.

24. The centrifuge blood processing system of claim 23 wherein said control circuit initiates at least one illumination session commencing a selected rotation from said initial zero position.

25. The centrifuge blood processing system of claim 23 wherein said initial zero position can be calibrated at any position along the rotation of the separation chamber.

26. The monitoring system of claim 21 further comprising a Halls effect sensor coupled to said separation chamber, said Halls effect sensor communicating a signal related to a rotational position of said separation chamber to said dedicated control circuit.

27. The centrifuge blood processing system of claim 21 further comprising a user stroboscopic light source, said user stroboscopic light source being controlled by a user control circuit in response to signals from said encoder.

28. The monitoring system of claim 27 further comprising a Halls effect sensor coupled to said separation chamber, said Halls effect sensor communicating a signal related to a rotational position of said separation chamber to said dedicated control circuit.

29. A centrifuge blood processing system for separating fluid components comprising
a separation chamber
a motor coupled to said separation chamber for rotating said chamber about a central rotation axis,
a plurality of pumps for controlling fluid flow within said separation chamber,
a controller in electrical communication with said pumps and said motor, said controller producing commands controlling said pumps and said motor, and
a monitoring system in electrical communication with said controller and monitoring fluid in said separation chamber, said monitoring system comprising:
a first light source in optical communication with said blood processing system for providing an incident light beam for illuminating an observation region wherein at least part of said separation chamber can be observed at selected times, thereby generating light transmitted, scattered or both from said observation region;
a light collection element in optical communication with said centrifuge blood processing system for collecting at least a portion of said light transmitted, scattered or both from said observation region;
a programmable controller for providing an operational procedure for said monitoring system; and
an independent dedicated control circuit in electrical communication with said programmable controller and electrically coupled to said first light source, said dedicated control circuit comprising means for receiving command parameters from said controller and means for energizing said first light source at a first selected rotation and de-energizing said first light source after a selected duration.

30. The centrifuge blood processing system of claim 29 wherein said first light source is an upper light source, and further comprising a lower light source and a monitoring camera, said camera having a shutter apparatus, and wherein said control circuit can control each of said upper light source, said lower light source and said monitoring camera.

31. A centrifuge blood processing system for separating fluid components comprising
a separation chamber
a motor coupled to said separation chamber for rotating said chamber about a central rotation axis,
a plurality of pumps for controlling fluid flow within said separation chamber,
a controller in electrical communication with said pumps and said motor, said controller producing commands controlling said pumps and said motor, and
a monitoring system in electrical communication with said controller and monitoring fluid in said separation chamber, said monitoring system comprising:
a first light source in optical communication with said blood processing system for providing an incident light beam for illuminating an observation region wherein at least part of said separation chamber can be observed at selected times, thereby generating light transmitted, scattered or both from said observation region;
a light collection element in optical communication with said centrifuge blood processing system for collecting at least a portion of said light transmitted, scattered or both from said observation region;
a programmable controller for providing an operational procedure for said monitoring system; and
an independent dedicated control circuit in electrical communication with said programmable controller and electrically coupled to said first light source, said dedicated control circuit comprising means for receiving command parameters from said controller and a first timer limiting the duration of a period of illumination from said first light source.

32. The centrifuge blood processing system of claim 31 wherein said first light source comprises light-emitting diodes (LEDs) and wherein said duration of illumination is limited to prevent failure of said LEDs.

33. The centrifuge blood processing system of claim 31 further comprising a second timer providing a minimum period between periods of illumination.

34. The centrifuge blood processing system of claim 33 wherein said first light source comprises light-emitting diodes (LEDs) and wherein said duration of illumination and said minimum period between periods of illumination are selected to prevent failure of said LEDs.

35. A centrifuge blood processing system for separating fluid components comprising
a separation chamber
a motor coupled to said separation chamber for rotating said chamber about a central rotation axis,
a plurality of pumps for controlling fluid flow within said separation chamber,
a controller in electrical communication with said pumps and said motor, said controller producing commands controlling said pumps and said motor, and
a monitoring system in electrical communication with said controller and monitoring fluid in said separation chamber, said monitoring system comprising:
a first light source in optical communication with said blood processing system for providing an incident light beam for illuminating an observation region wherein at least part of said separation chamber can be observed at selected times, thereby generating light transmitted, scattered or both from said observation region;
a light collection element in optical communication with said centrifuge blood processing system for collecting at least a portion of said light transmitted, scattered or both from said observation region;
a programmable controller for providing an operational procedure for said monitoring system; and an independent dedicated control circuit in electrical communication with said programmable controller and electrically coupled to said first light source, said dedicated control circuit comprising means for receiving command parameters from said controller and means for controlling a plurality of sessions comprising delays and periods of illumination.

36. The centrifuge blood processing system of claim 35 wherein said dedicated control circuit combines overlapping periods of illumination into a combined period of illumination.

37. The centrifuge blood processing system of claim 36 further comprising a first timer limiting the duration of a period of illumination from said first light source.

38. The centrifuge blood processing system of claim 37 wherein said first light source comprises light-emitting diodes (LEDs) and wherein said duration of illumination is limited to prevent failure of said LEDs.

39. The centrifuge blood processing system of claim 38 further comprising a second timer providing a minimum period between periods of illumination.

40. The centrifuge blood processing system of claim 39 wherein said first light source comprises light-emitting diodes (LEDs) and wherein said duration of illumination and said minimum period between periods of illumination are selected to prevent failure of said LEDs.

41. A method of controlling a centrifuge blood processing system for separating fluid components and having a separation chamber rotating about a central rotation axis, comprising:
providing a programmable controller for controlling functions of said blood processing system,
providing a first light source in optical communication with said separation chamber,
illuminating an observation region on said separation chamber, thereby generating light transmitted, scattered or both from said observation region;
collecting at least a portion of said light transmitted, scattered or both from said observation region through an independent dedicated control circuit in electrical communication with said programmable controller and electrically coupled to said first light source, said dedicated control circuit receiving command parameters from said controller and energizing said first light source at a first selected rotation and de-energizing said first light source after a selected duration.

42. The method of claim 41 further comprising communicating a signal related to a rotational position of said separation chamber to said dedicated control circuit.

43. The method of claim 41 further comprising identifying an initial zero position of said separation chamber.

44. The method of claim 43 wherein said dedicated control circuit initiates at least one illumination session commencing a selected rotation from said initial zero position.

45. The method of claim 43 further comprising calibrating said zero position at any position along the rotation of the separation chamber.

46. The method of claim 41 wherein said first light source is an upper light source, and further comprising a lower light source and a monitoring camera, said camera having a shutter apparatus, said method further comprising controlling each of said upper light source, said lower light source and said monitoring camera through said dedicated control circuit.

47. The method of claim 41 further comprising providing a user stroboscopic light source.

48. The method of claim 41 further comprising limiting the duration of a period of illumination from said first light source.

49. The method of claim 48 wherein said first light source comprises light-emitting diodes (LEDs), said method further comprising limiting said duration of illumination to prevent failure of said LEDs.

50. The method of claim 48 further comprising providing a minimum period between periods of illumination.

51. The method of claim 50 wherein said first light source comprises light-emitting diodes (LEDs), said method further comprising selecting said duration of illumination and said minimum period between periods of illumination to prevent failure of said LEDs.

52. The method of claim 41 wherein a period of illumination controlled by said dedicated control circuit constitutes a session, and said method further comprises controlling a plurality of sessions.

53. The method of claim 52 further comprising combining overlapping periods of illumination into a combined period of illumination.

54. The method of claim 53 further comprising limiting the duration of a period of illumination from said first light source.

55. The method of claim 54 wherein said first light source comprises light-emitting diodes (LEDs), said method further comprising limiting said duration of illumination to prevent failure of said LEDs.

56. The method of claim 55 further comprising providing a minimum period between periods of illumination.

57. The method of claim 56 wherein said first light source comprises light-emitting diodes (LEDs), said method further comprising selecting said duration of illumination and said minimum period between periods of illumination to prevent failure of said LEDs.

58. A method of controlling a centrifuge blood processing system for separating fluid components and having a separation chamber rotating about a central rotation axis, comprising:
providing a programmable controller for controlling functions of said blood processing system,
providing a first light source in optical communication with said separation chamber, illuminating at least part of said separation chamber at selected times through an observation region, thereby generating light transmitted, scattered or both from said observation region;
collecting at least a portion of said light transmitted, scattered or both from said observation region through an independent dedicated control circuit in electrical communication with said programmable controller and electrically coupled to said first light source, said dedicated control circuit receiving command parameters from said controller and providing a signal to said first light source to completely control the initiation, duration, intensity and termination of illumination from said first light source.

59. A centrifuge blood processing system for separating fluid components comprising
a separation chamber
a motor coupled to said separation chamber for rotating said chamber about a central rotation axis,
a plurality of pumps for controlling fluid flow within said separation chamber,
a controller in electrical communication with said pumps and said motor, said controller producing commands controlling said pumps and said motor, and a monitoring system in electrical communication with said controller and monitoring fluid in said separation chamber, said monitoring system comprising:

a first light source in optical communication with said blood processing system for providing an incident light beam for illuminating an observation region on said centrifugal blood processing system, thereby generating light transmitted, scattered or both from said observation region;

a light collection element in optical communication with said centrifuge blood processing system for collecting at least a portion of said light transmitted, scattered or both from said observation region;

a programmable controller for providing an operational procedure for said monitoring system; and a first timer limiting the duration of a period of illumination from said first light source, and wherein said first light source comprises light-emitting diodes (LEDs) and said duration of illumination is limited to prevent failure of said LEDs.

60. The centrifuge blood processing system of claim 59 further comprising a second timer providing a minimum period between periods of illumination and said minimum period between periods of illumination is selected to prevent failure of said LEDs.

61. The centrifuge blood processing system of claim 59 wherein said controller controls a plurality of sessions comprising delays and periods of illumination.

62. The centrifuge blood processing system of claim 61 wherein said controller combines overlapping periods of illumination into a combined period of illumination.

63. The centrifuge blood processing system of claim 62 further comprising a second timer providing a minimum period between periods of illumination and said minimum period between periods of illumination are selected to prevent failure of said LEDs.

* * * * *